US012090224B2

(12) United States Patent
Faig et al.

(10) Patent No.: US 12,090,224 B2
(45) Date of Patent: Sep. 17, 2024

(54) COSMETIC COMPOSITION COMPRISING HIGH AMOUNTS OF CERAMIDE-NP

(71) Applicant: L'OREAL, Paris (FR)

(72) Inventors: Jonathan James Faig, Sayreville, NJ (US); Susan Halpern Chirch, Basking Ridge, NJ (US); Angelike Galdi, Westfield, NJ (US); Yon Jae Yoon, Roselle, NJ (US); David Chan, Oradell, NJ (US)

(73) Assignee: L'OREAL, Paris (FR)

( * ) Notice: Subject to any disclaimer, the term of this patent is extended or adjusted under 35 U.S.C. 154(b) by 0 days.

(21) Appl. No.: 18/050,496

(22) Filed: Oct. 28, 2022

(65) Prior Publication Data
US 2023/0134147 A1   May 4, 2023

Related U.S. Application Data

(60) Provisional application No. 63/273,962, filed on Oct. 31, 2021.

(30) Foreign Application Priority Data

Jan. 31, 2022 (FR) ..................................... 2200818

(51) Int. Cl.
A61K 8/68      (2006.01)
A61K 8/06      (2006.01)
A61K 8/36      (2006.01)
A61K 8/84      (2006.01)
A61K 8/92      (2006.01)
A61Q 19/00     (2006.01)

(52) U.S. Cl.
CPC .............. A61K 8/68 (2013.01); A61K 8/062 (2013.01); A61K 8/361 (2013.01); A61K 8/84 (2013.01); A61K 8/92 (2013.01); A61Q 19/00 (2013.01); A61K 2800/48 (2013.01)

(58) Field of Classification Search
CPC .......... A61K 8/68; A61K 8/062; A61K 8/361; A61K 8/84; A61K 8/92; A61K 2800/48; A61K 8/342; A61K 8/375; A61K 8/60; A61K 8/8152; A61Q 19/00
See application file for complete search history.

(56) References Cited

U.S. PATENT DOCUMENTS

| 10,449,133 | B1  | 10/2019 | Faig et al. |
| 10,898,496 | B2  | 1/2021  | Simard |
| 10,973,749 | B2* | 4/2021  | Sverdlove ............ A61K 8/676 |
| 11,058,614 | B2  | 7/2021  | Choi et al. |
| 2002/0019547 | A1 | 2/2002 | Tuloup et al. |
| 2002/0058010 | A1 | 5/2002 | Picard-Lesboueyries et al. |
| 2002/0182238 | A1 | 12/2002 | Creton |
| 2002/0197289 | A1 | 12/2002 | Chevalier et al. |
| 2003/0215413 | A1 | 11/2003 | Fares et al. |
| 2004/0137024 | A1 | 7/2004 | Abriat et al. |
| 2004/0162272 | A1 | 8/2004 | Hansenne et al. |
| 2005/0191337 | A1 | 9/2005 | Gueret |
| 2006/0026775 | A1 | 2/2006 | Rozot et al. |
| 2007/0015840 | A1 | 1/2007 | Dalko et al. |
| 2007/0202065 | A1 | 8/2007 | Devin-Baudoin et al. |
| 2007/0202203 | A1 | 8/2007 | Amar |
| 2007/0248633 | A1 | 10/2007 | Baldo |
| 2008/0050333 | A1 | 2/2008 | Lemoine et al. |
| 2008/0131391 | A1 | 6/2008 | Ellington et al. |
| 2008/0153839 | A1 | 6/2008 | Cotton et al. |
| 2008/0159970 | A1 | 7/2008 | Willemin |
| 2008/0226756 | A1 | 9/2008 | Willemin et al. |
| 2008/0293962 | A1 | 11/2008 | Dalko et al. |
| 2009/0016971 | A1 | 1/2009 | Gaudry et al. |
| 2009/0016974 | A1 | 1/2009 | Pruche et al. |
| 2009/0018200 | A1 | 1/2009 | Willemin et al. |
| 2009/0041691 | A1 | 2/2009 | Candau et al. |
| 2009/0285868 | A1 | 11/2009 | Richard et al. |
| 2009/0317430 | A1 | 12/2009 | Cassin et al. |
| 2010/0086502 | A1 | 4/2010 | Lucet-Levannier et al. |
| 2010/0112100 | A1 | 5/2010 | Willemin et al. |
| 2010/0189675 | A1 | 7/2010 | Pelletier |
| 2010/0197805 | A1* | 8/2010 | Cassin ..................... A61K 8/31 514/772.1 |
| 2011/0021438 | A1 | 1/2011 | Dalko et al. |
| 2011/0130704 | A1 | 6/2011 | Baldo et al. |
| 2013/0259912 | A1 | 10/2013 | Suzuki et al. |

(Continued)

FOREIGN PATENT DOCUMENTS

| DE | 102017201050 A1 | 7/2018 |
| EP | 0955038 B1 | 7/2003 |
| EP | 3082974 A1 | 10/2016 |
| FR | 3059545 A1 | 6/2018 |
| JP | 2021113155 A | 8/2021 |
| WO | 9513791 A1 | 5/1995 |
| WO | 9616635 A1 | 6/1996 |
| WO | 2011030308 A1 | 3/2011 |
| WO | 2018177730 | 10/2018 |
| WO | 2021180400 A1 | 9/2021 |

OTHER PUBLICATIONS

"Beiersdorf Personalizes Face Care with Launch of New Brand O.W.N." Newsroom-Press Releases, 2021, pp. 1-2.

(Continued)

Primary Examiner — Benjamin J Packard
Assistant Examiner — Joshua A Atkinson
(74) Attorney, Agent, or Firm — POLSINELLI PC

(57) ABSTRACT

The present disclosure relates to stable cosmetic compositions containing high amounts of ceramide NP. The cosmetic compositions further include high amounts of hydroxypropyl tetrahydropyrantriol, a plurality of emulsifiers, fatty alcohols, fatty compounds, and water. Methods for stabilizing the cosmetic compositions containing high amounts of ceramide NP and methods for treating the skin with the cosmetic compositions is also described.

20 Claims, No Drawings

(56) References Cited

U.S. PATENT DOCUMENTS

| | | |
|---|---|---|
| 2013/0344015 A1 | 12/2013 | Gaudry et al. |
| 2014/0287005 A1 | 9/2014 | Chevalier et al. |
| 2015/0047664 A1 | 2/2015 | Samain et al. |
| 2015/0157539 A1 | 6/2015 | Shimizu et al. |
| 2015/0174047 A1 | 6/2015 | Chiou et al. |
| 2015/0174050 A1 | 6/2015 | Lu et al. |
| 2015/0265504 A1 | 9/2015 | Crane et al. |
| 2016/0213599 A1 | 7/2016 | Devie |
| 2016/0220308 A1 | 8/2016 | Khormaei et al. |
| 2016/0220804 A1 | 8/2016 | Khormaei et al. |
| 2017/0151538 A1 | 6/2017 | Balooch et al. |
| 2017/0154372 A1 | 6/2017 | Balooch et al. |
| 2017/0326045 A1 | 11/2017 | Lorant et al. |
| 2017/0348221 A1 | 12/2017 | Maruyama et al. |
| 2018/0085721 A1 | 3/2018 | Rinaldis et al. |
| 2018/0243182 A1 | 8/2018 | Ricard et al. |
| 2018/0344609 A1 | 12/2018 | Lu et al. |
| 2019/0038539 A1* | 2/2019 | Garruto .................. A61Q 19/00 |
| 2019/0110967 A1* | 4/2019 | Chiou .................... A61K 8/922 |
| 2019/0159980 A1 | 5/2019 | Chen et al. |
| 2020/0211078 A1 | 7/2020 | Balooch et al. |
| 2020/0246228 A1* | 8/2020 | Maczkiewitz ......... A61K 8/342 |
| 2020/0253853 A1 | 8/2020 | Lu et al. |
| 2020/0277093 A1 | 9/2020 | Besen et al. |
| 2021/0015719 A1 | 1/2021 | Lu et al. |

OTHER PUBLICATIONS

Kacey Culliney, "Beiersdorf files patent on AI skin profiling and product recommendation method," 2021, pp. 1-3.

\* cited by examiner

COSMETIC COMPOSITION COMPRISING HIGH AMOUNTS OF CERAMIDE-NP

CROSS-REFERENCE TO RELATED APPLICATIONS

This application claims benefit of U.S. Ser. No. 63/273,962 filed Oct. 31, 2021, and benefit of French Application No. FR 2200818, filed on Jan. 31, 2022, which are incorporated herein by reference in their entirety.

FIELD OF THE DISCLOSURE

The instant disclosure relates to stable cosmetic compositions that include high amounts of ceramide-NP; and to methods for stabilizing cosmetic compositions containing high amounts of ceramide-NP. The instant disclosure also describes methods for treating skin with the cosmetic compositions.

SUMMARY

In an aspect, the present disclosure is directed to, among other things, cosmetic compositions including a surprisingly high amount of ceramide-NP. In addition, the compositions also include a surprisingly high amount of hydroxypropyl tetrahydropyrantriol. These active ingredients provide a myriad of cosmetic benefits to the skin but have historically been very difficult to solubilize and stabilize, especially in high amounts. The inventors of the instant disclosure developed, among other things, surprisingly stable compositions that include high amounts of ceramide-NP and surprisingly high amounts of hydroxypropyl tetrahydropyrantriol. Due to the high amounts of ceramide-NP, the cosmetic compositions provide exceptional cosmetic properties to the skin, for example, hydration of skin and maintenance of moisture balance, alleviation/reduction of itching, chronic dryness, peeling, and scaling. Ceramide-NP is also helpful for reinforcing the natural lipid barrier of skin, which helps treat dry and aging skin. Due to the high amounts of hydroxypropyl tetrahydropyrantriol, the cosmetic compositions provide benefits such as reduction of fine lines and wrinkles, improving production of hyaluronic acid via stimulation of glycosaminoglycan (GAG) synthesis, softening of stratum corneum to relieve cumulative stress on the epidermis and dermis, etc.

In an aspect, the present disclosure is directed to, among other things, a cosmetic composition in the form of an oil in water emulsion. In an embodiment, the cosmetic composition includes:
(a) ceramide NP;
(b) water;
(c) one or more first emulsifiers chosen from polyglycerol-based emulsifiers;
(d) one or more second emulsifiers chosen from glyceryl esters having an HLB (hydrophilic-lipophilic balance) of about 3 to about 6;
(e) one or more third emulsifiers chosen from ethoxylated fatty acids;
(f) one or more fatty alcohols; and
(g) one or more non-triglyceride and non-aromatic fatty compounds;
wherein the composition is an oil-in-water emulsion and all percentages by weight are based on the total weight of the composition.

In certain embodiments, the cosmetic compositions include one or more of the following weight ratios for (a) and (c)-(g):
a weight ratio of the one or more first emulsifiers chosen from polyglycerol-based emulsifiers to the ceramide NP of about 1.5:1 to about 8:1 ((c):(a)); and/or
a weight ratio of the one or more second emulsifiers chosen from glyceryl esters having an HLB of about 3 to about 6 to the ceramide NP of about 0.8:1 to about 4:1 ((d):(a)); and/or
a weight ratio of the one or more third emulsifiers chosen from ethoxylated fatty acids to the ceramide NP of about 0.7:1 to about 4:1 ((e):(a)); and/or
a weight ratio of the one or more fatty alcohols to the ceramide NP of about 0.7:1 to about 4:1 ((f):(a)); and/or
a weight ratio of the one or more non-triglyceride and non-aromatic fatty compounds to the ceramide NP of about 4:1 to about 20:1 ((g):(a)).

Nonlimiting examples of polyglycerol-based emulsifiers include polyglyceryl 10-stearate, polyglyceryl-3-caprate, polyglyceryl-3-diisostearate, polyglyceryl-3 methylglucose distearate, or a mixture thereof.

Nonlimiting examples of glyceryl esters having an HLB of about 3 to about 8 include glyceryl behenate, glyceryl erucate, glyceryl hydroxystearate, glyceryl isostearate, glyceryl lanolate, glyceryl laurate, glyceryl linoleate, glyceryl myristate, glyceryl palmitate lactate, glyceryl stearate, glyceryl distearate, glyceryl laurate, or a mixture thereof. In at least one instance the glyceryl ester comprises glyceryl stearate, glyceryl ricinoleate, and mixtures thereof Nonlimiting examples of ethoxylated fatty acids having from 40 to 100 propylene oxide groups and the fatty acid chain ranging from 12 to 24 carbons include lauric acid, tridecylic acid, myristic acid, pentadecylic acid, palmitic acid, margaric acid, stearic acid, nonadecylic aciud, arachidic acid, heniicosylic acid, behenic acid, tricosylic cid, and lignoceric acid, especially containing 40 to 100 propylene oxide groups.

Nonlimiting example of fatty alcohols include those having from 12 to 24 carbon atoms. For example, fatty alcohols chosen from cetyl alcohol, stearyl alcohol, cetearyl alcohol, behenyl alcohol, lauryl alcohol, myristic or myristyl alcohol, arachidyl alcohol, lignoceryl alcohol, and mixtures thereof.

Nonlimiting examples of non-triglyceride and non-aromatic fatty compounds include fatty esters (isopropyl myristate, sorbitan isostearate), sarcosinates, for instance an acyl sarcosinate, plant and/or vegetable oils, and mixtures thereof. Non-limiting examples of sarcosinates can be selected from the group consisting of sodium lauroyl sarcosinate, sodium cocoyl sarcosinate, sodium myristoyl sarcosinate, sodium caproyl sarcosinate, TEA-cocoyl sarcosinate, ammonium cocoyl sarcosinate, ammonium lauroyl sarcosinate, dimer dilinoleyl bis-lauroylglutamate/lauroylsarcosinate, disodium lauroamphodiacetate lauroyl sarcosinate, isopropyl lauroyl sarcosinate, potassium cocoyl sarcosinate, potassium lauroyl sarcosinate, sodium cocoyl sarcosinate, sodium lauroyl sarcosinate, sodium myristoyl sarcosinate, sodium oleoyl sarcosinate, sodium palmitoyl sarcosinate, TEA-cocoyl sarcosinate, TEA-lauroyl sarcosinate, TEA-oleoyl sarcosinate, TEA-palm kernel sarcosinate, and combinations thereof.

In various embodiments, the cosmetic compositions may optionally include one or more thickening polymers. Nonlimiting examples of various types of thickening polymers include polyacrylate, polymethacrylate, polyethylacrylate, and polyacrylamide, acrylic acid/acrylonitrogens copolymer, acrylates/steareth-20 itaconate copolymer, acrylates/ ceteth-20 itaconate copolymer, acrylates/aminoacrylates/C10-30 alkyl PEG-20 Itaconate copolymer, acrylates/aminoacrylates copolymer, acrylates/steareth-20 methacrylate copolymer, acrylates/beheneth-25 methacrylate copolymer, acrylates/steareth-20 methacrylate crosspolymer, acrylates/beheneth-25 methacrylate/HEMA crosspolymer, acrylates/vinyl neodecanoate crosspolymer, acrylates/vinyl isodecanoate crosspolymer, acrylates/palmeth-25 acrylate copolymer, acrylic acid/acrylamidomethyl propane sulfonic acid copolymer, and acrylates/C10-C30 alkyl acrylate crosspolymer, carbomers, hydrophobically modified polypolyacrylates; hydrophobically modified polyacrylic acids, hydrophobically modified polyacrylamides; hydrophobically modified polyethers wherein these materials may have a hydrophobe that can be selected from cetyl, stearyl, oleayl, and combinations thereof, acrylamide/ammonium acrylate copolymer; acrylamide/sodium acryloyldimethyl taurate copolymer/isohexadecane/polysorbate 80, ammonium acryloyldimethyltaurate/VP copolymer, Sodium Acrylate/Sodium Acryloyldimethyl Taurate Copolymer, acrylates copolymer, Acrylates Crosspolymer-4, Acrylates Crosspolymer-3, acrylates/beheneth-25 methacrylate copolymer, acrylates/C10-C30 alkyl acrylate crosspolymer, acrylates/steareth-20 itaconate copolymer, ammonium polyacrylate/Isohexadecane/PEG-40 castor oil; sodium carbomer, crosslinked polyvinylpyrrolidone (PVP), polyacrylamide/C13-14 isoparaffin/laureth-7, polyacrylate 13/polyisobutene/polysorbate 20, polyacrylate crosspolymer-6, polyamide-3, polyquaternium-37, Acrylamide/Sodium Acryloyldimethyltaurate/Acrylic Acid Copolymer, sodium acrylate/acryloyldimethyltaurate, sodium polyacrylate, and a mixture thereof.

In various embodiments, the cosmetic compositions may optionally include one or more water soluble solvents. Non-limiting examples of water-soluble solvents include, for example, glycerin, alcohols (for example, $C_{1-30}$, $C_{1-15}$, $C_{1-10}$, or $C_{1-4}$ alcohols), organic solvents, polyols, glycols, and a mixture thereof.

In various embodiments, silicones can optionally be included in the cosmetic compositions but preferably the compositions are free or essentially free from silicones. Silicones are synthetic polymers made up of repeating units of siloxane, elemental silicon and oxygen, combined with other elements, most often carbon and hydrogen. Thus, silicones are also called polysiloxanes. In some instances, the cosmetic compositions of the instant case can be free or essentially free from dimethicones, amomdimethicones, dimethiconols, cyclosiloxanes, siloxanes, etc.

In an embodiment, the cosmetic compositions form part of a kit comprising a cosmetic composition according to the instant disclosure and one or more separately contained compositions. In an embodiment, the compositions are received in a kit, which is a device, for example, a device that dispenses the cosmetic compositions. In an embodiment, the device mixes the cosmetic compositions with one or more additional cosmetic compositions before dispensing the mixture. Even though high amounts of ceramide-NP are included in the cosmetic compositions, the compositions are unique in that they are compatible with other cosmetic compositions, in particular, other cosmetic compositions for treating the skin.

Another aspect of the instant disclosure relates to methods for stabilizing cosmetic compositions having high amounts of ceramide-NP. These methods, as describe throughout the disclosure, comprise combining these ingredients to prepare the compositions of the instant disclosure.

Another aspect of the instant disclosure relates to methods for treating skin. The methods include applying the cosmetic composition according to the instant disclosure to the skin. In an embodiment, the methods hydrate the skin and/or provide maintenance of moisture balance, alleviate/reduce itching, chronic dryness, peeling, and scaling; and improve the natural lipid barrier of skin, which helps treat dry and aging skin. In certain embodiments, when the composition includes hydroxypropyl tetrahydropyrantriol, the methods also reduce the appearance of fine lines and wrinkles, improve production of hyaluronic acid via stimulation of glycosaminoglycan (GAG) synthesis, softening of stratum corneum to relieve cumulative stress on the epidermis and dermis, etc.

Other features and iterations of the invention are described in more detail below.

DETAILED DESCRIPTION OF THE INVENTION

A common problem associated with formulating compositions, especially composition comprising multiple components, is ensuring physical stability, chemical stability, solubility, and the like. Many additives for food, cosmetics, personal care, and household products into which they are incorporated are difficult to stabilize and solubilize, especially when used in high amounts. The consequence of stability and solubility problems is significant. For example, stability problems can cause partial, if not complete, loss of product integrity, color loss, malodor, viscosity changes, etc. Stability problems can also cause an increased or a decreased amount of the component in question to be applied. With respect to active ingredients, stability problems reduce or eliminate activity, and prevent the active ingredients from reaching their intended target in the desired amount.

With aging, the outer skin layer (epidermis) thins, even though the number of cell layers remains unchanged. The number of pigment-containing cells (melanocytes), however, decreases. Therefore, the skin appears pale and translucent. Large pigmented spots (age spots, liver spots, or lentigos) may appear in sun-exposed areas. Changes in the connective tissue reduce the skin's strength and elasticity. This is known as elastosis. It is more noticeable in sun-exposed areas (solar elastosis). Elastosis produces the leathery, weather-beaten appearance common to farmers, sailors, and others who spend a large amount of time outdoors. Dehydration increases the risk of skin injury. Poor nutrition can also negatively influence the skin, causing dryness, rash, and puffiness.

Human skin acts as a primary barrier between the body and its environment. Crucial for this skin barrier function is the lipid matrix in the outermost layer of the skin (epidermis), the stratum corneum (SC). Two of its functions are (1) to prevent excessive water loss through the epidermis and (2) to avoid that compounds from the environment permeate into the viable epidermal and dermal layers and thereby provoke an immune response. The composition of the SC lipid matrix is dominated by three lipid classes: cholesterol, free fatty acids, and ceramides. These lipids adopt a highly ordered, 3-dimensional structure of stacked densely packed lipid layers (lipid lamellae): the lateral and lamellar lipid organization. The way in which these lipids are ordered depends on the composition of the lipids. One very common skin disease in which the SC lipid barrier is affected is atopic dermatitis (AD).

What is needed, among other things, are compositions which include high amounts of ceramide NP that replenishes the ceramides in the lipid matrix in the outermost layer of the skin, and that reduce the effects of aging, improve the radiancy and smoothness of the skin, and the like.

In an aspect, the present disclosure is directed to, among other things, a stable cosmetic composition that includes high amounts of ceramide NP; and to methods for stabilizing cosmetic compositions containing high amounts of ceramide-NP. In an embodiment, the compositions include:
(a) ceramide NP;
(b) water;
(c) one or more first emulsifiers chosen from polyglycerol-based emulsifiers;
(d) one or more second emulsifiers chosen from glyceryl esters having an HLB (hydrophilic-lipophilic balance) of about 3 to about 6;
(e) one or more third emulsifiers chosen from ethoxylated fatty acids;
(f) one or more fatty alcohols; and
(g) one or more non-triglyceride and non-aromatic fatty compounds;
wherein the composition is an oil in water emulsion and the composition comprises one or more of the following weight ratios;
a weight ratio of the one or more first emulsifiers chosen from polyglycerol-based emulsifiers to the ceramide NP of about 1.5:1 to about 8:1 ((c):(a)); and/or
a weight ratio of the one or more second emulsifiers chosen from glyceryl esters having an HLB of about 3 to about 6 to the ceramide NP of about 0.8:1 to about 4:1 ((d):(a)); and/or
a weight ratio of the one or more third emulsifiers chosen from ethoxylated fatty acids to the ceramide NP of about 0.7:1 to about 4:1 ((e):(a)); and/or
a weight ratio of the one or more fatty alcohols to the ceramide NP of about 0.7:1 to about 4:1 ((f):(a));
a weight ratio of the one or more non-triglyceride and non-aromatic fatty compounds to the ceramide NP of about 4:1 to about 20:1 ((g):(a)).

The compositions may further include other components, as described throughout the disclosure, for example: (i) one or more thickening polymers; and/or (j) one or more water-soluble solvents; and/or (k) one or more miscellaneous ingredients. In certain embodiments, the compositions may optionally include one or more silicones, but preferably the compositions are free or essentially free from silicones.

In an aspect, the present disclosure is directed to, among other things, a stable cosmetic composition that includes high amounts of ceramide NP; and to methods for stabilizing cosmetic compositions containing high amounts of ceramide-NP. In an embodiment, the compositions include:
(a) about 0.1 to about 5 wt. % of ceramide NP;
(b) water;
(c) about 0.5 to about 5 wt. % of one or more first emulsifiers chosen from polyglycerol-based emulsifiers;
(d) about 0.5 to about 5 wt. % of one or more second emulsifiers chosen from glyceryl esters having an HLB of about 3 to about 6;
(e) about 0.5 to about 5 wt. % of one or more third emulsifiers chosen from ethoxylated fatty acids;
(f) about 0.2 to about 5 wt. % of one or more fatty alcohols; and
(g) about 4 to about 20 wt. % of one or more non-triglyceride and non-aromatic fatty compounds;
wherein the composition is an oil in water emulsion and all percentages by weight are based on the total weight of the composition.

The compositions may further include other components, as described throughout the disclosure, for example: (i) one or more thickening polymers; and/or (j) one or more water-soluble solvents; and/or (k) one or more miscellaneous ingredients. In certain embodiments, the compositions may optionally include one or more silicones, but preferably the compositions are free or essentially free from silicones.

In an aspect, the present disclosure is directed to, among other things, a stable cosmetic composition that includes high amounts of ceramide NP; and to methods for stabilizing cosmetic compositions containing high amounts of ceramide-NP. In an embodiment, the compositions include:
(a) about 0.1 to about 5 wt. % of ceramide NP;
(b) water;
(c) about 0.5 to about 5 wt. % of one or more first emulsifiers chosen from polyglycerol-based emulsifiers;
(d) about 0.5 to about 5 wt. % of one or more second emulsifiers chosen from glyceryl esters having an HLB of about 3 to about 6;
(e) about 0.5 to about 5 wt. % of one or more third emulsifiers chosen from ethoxylated fatty acids;
(f) about 0.2 to about 5 wt. % of one or more fatty alcohols; and
(g) about 4 to about 20 wt. % of one or more non-triglyceride and non-aromatic fatty compounds;
wherein the composition is an oil in water emulsion and all percentages by weight are based on the total weight of the composition, provided that one or more of the following ratios apply:
a weight ratio of the one or more first emulsifiers chosen from polyglycerol-based emulsifiers to the ceramide NP of about 1.5:1 to about 8:1 ((c):(a)); and/or
a weight ratio of the one or more second emulsifiers chosen from glyceryl esters having an HLB of about 3 to about 6 to the ceramide NP of about 0.8:1 to about 4:1 ((d):(a)); and/or
a weight ratio of the one or more third emulsifiers chosen from ethoxylated fatty acids to the ceramide NP of about 0.7:1 to about 4:1 ((e):(a)); and/or
a weight ratio of the one or more fatty alcohols to the ceramide NP of about 0.7:1 to about 4:1 ((f):(a));
a weight ratio of the one or more non-triglyceride and non-aromatic fatty compounds to the ceramide NP of about 4:1 to about 20:1 ((g):(a)).

(a) Ceramide NP

Ceramide NP represents "(9Z)-N-[(2S,3S,4R)-1,3,4-trihydroxyoctadecan-2-yl]octadec-9-enamide." Ceramide NP consists of a phytosphingosine backbone N-acylated with a saturated fatty acid (stearic acid). Ceramide NP provides numerous benefits to the skin such as, rehydration of dry skin, reduction of itching, chronic dryness, relieving itching, reduction of peeling and scaling.

Generally, the amount of ceramide NP in the cosmetic compositions ranges from about 0.1 wt. % to about 5 wt. % based on the total weight of the composition. In various embodiments, the amounts of ceramide NP ranges from about 0.1 wt. % to about 4.0 wt. %, from about 0.1 to about 3 wt. %, from about 0.2 wt. % to about 5 wt. %, about 0.2 to about 4 wt. %, about 0.2 to about 2 wt. %, about 0.2 to about 3 wt. %, about 0.3 to about 5 wt. %, about 0.3 to about 4 wt. %, about 0.3 to about 3 wt. %, about 0.3 to about 2 wt. %, about 0.4 to about 5 wt. %, about 0.4 to about 4 wt. %, about 0.4 to about 3 wt. %, about 0.4 to about 2 wt. %, about 0.5 wt. % to about 5 wt. %, about 0.5 wt. %, about 4 wt. %, about 0.5 wt. % to about 3 wt. %, about 0.5 to about 2 wt. %, or 0.5 to about 1 wt. %, based on the total weight of the composition. In even further embodiments, the amount of ceramide NP is at least 0.1 wt. %, at least 0.2 wt. %, at least 0.3 wt. %, at least 0.4 wt. %, at least 0.5 wt. %, or at least 0.6 wt. % and can have a maximum of about 1, 2, 3, 4, or 5 wt. %, based on the total weight of the composition.

(b) Water

The amount of water in the composition of the instant disclosure can and will vary depending on the amount of the other components in the cosmetic composition. Nonetheless, in certain embodiments, the amount of water in the composition is from about 50 to about 90 wt. %, based on the total weight of the composition. In various embodiments, the amount of water in the cosmetic compositions is from about 55 to about 90 wt. %, about 60 to about 90 wt. %, about 65 to about 90 wt. %, about 70 to about 90 wt. %, about 60 to about 85 wt. %, about 65 to about 85 wt. %, about 70 to about 85 wt. %, about 60 to about 80 wt. %, about 65 to about 80 wt. %, or about 70 to about 80 wt. %, based on the total weight of the composition.

(c) Polyglycerol-Based Emulsifiers

The cosmetic composition of the instant disclosure includes one or more first emulsifiers chosen from polyglycerol-based emulsifiers. Nonlimiting examples include polyglyceryl 10-stearate, polyglyceryl-3-caprate, polyglyceryl-3-diisostearate, polyglyceryl-3 methylglucose distearate, or a mixture thereof. In various embodiments, the polyglycerol-based emulsifiers may be polyglycerol esters of fatty acids having a structure in accordance with the following formula:

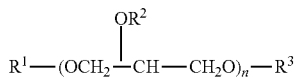

wherein n is from 2 to 20 or from 2 to 10 or from 2 to 5, or is 2, 3, 4, 5, 6, 7, 8, 9, or 10, and $R^1$, $R^2$ and $R^3$ each may independently be a fatty acid moiety or hydrogen, provided that at least one of $R^1$, $R^2$, and $R^3$ is a fatty acid moiety. For instance, $R^1$, $R^2$ and $R^3$ may be saturated or unsaturated, straight or branched, and have a length of $C_1$-$C_{40}$, $C_1$-$C_{30}$, $C_1$-$C_{25}$, or $C_1$-$C_{20}$, $C_1$-$C_{16}$, or $C_1$-$C_{10}$. Additionally, non-limiting examples of nonionic polyglycerol esters of fatty acids include polyglyceryl-4 caprylate/caprate, polyglyceryl-10 caprylate/caprate, polyglyceryl-4 caprate, polyglyceryl-10 caprate, polyglyceryl-4 laurate, polyglyceryl-5 laurate, polyglyceryl-6 laurate, polyglyceryl-10 laurate, polyglyceryl-10 cocoate, polyglyceryl-10 myristate, polyglyceryl-10 oleate, polyglyceryl-10 stearate, and mixtures thereof.

In certain embodiments, the polyglycerol-based emulsifier may be chosen from polyglyceryl esters of C12-22 saturated, unsaturated and branched chain fatty acids, such as polyglyceryl-4 isostearate, polyglyceryl-3 oleate, polyglyceryl-2-sesquioleate, triglyceryl diisostearate, diglyceryl monooleate, tetraglyceryl monooleate, and mixtures thereof. Non-limiting examples of glyceryl esters can include glyceryl caprylate, glyceryl caprate, glyceryl cocoate, glyceryl laurate, and combinations thereof.

In some embodiments, particularly useful polyglycerol-based emulsifiers include polyglyceryl methylglucose surfactants, such as polyglyceryl-3 methylglucose distearate, polyglyceryl-6 methylglucose distearate, polyglyceryl-10 methyl glucose distearate, and mixtures thereof.

The amount of the one or more first emulsifier chosen from polyglycerol-based emulsifiers varies but, in some embodiments, is from about 0.5 wt. % to about 5 wt. % based on the total weight of the composition. In various embodiments, the amount of the one or more first emulsifier chosen from polyglycerol-based emulsifiers is from about 0.5 wt. % to about 4 wt. %, about 0.5 to about 3 wt. %, about 0.5 to about 2 wt. %, about 0.6 to about 5 wt. %, about 0.6 to about 4 wt. %, about 0.6 to about 3 wt. %, about 0.6 to about 2 wt. %, about 0.8 to about 4 wt. %, about 0.8 wt. % about 3 wt. %, or about 0.8 to about 2 wt. %, based on the total weight of the composition.

(d) Glyceryl Esters Having an HLB of About 3 to About 6

The composition of the instant disclosure includes one or more second emulsifier(s) chosen from glyceryl ester having a HLB of about 3 to about 6. These are different from the polyglycerol-based emulsifiers discussed above. Suitable non-limiting examples of glyceryl esters having an HLB of about 3 to about 6 are chosen from glyceryl behenate, glyceryl erucate, glyceryl hydroxystearate, glyceryl isostearate, glyceryl lanolate, glyceryl laurate, glyceryl linoleate, glyceryl myristate, glyceryl oleate, glyceryl stearate, glyceryl dioleate, glyceryl distearate, or a mixture thereof. In at least one instance, the glyceryl ester comprises glyceryl stearate, glyceryl ricinoleate, or a mixture thereof.

In some instances, the glyceryl esters may be chosen from esters of an oligomeric glycerol, arachidyl propionate, phytosterol esters, triglycerides of fatty acids and derivatives thereof, noncrosslinked polyesters resulting from the poly condensation between a linear or branched C4-C50 dicarboxylic acid or polycarboxylic acid and a C2-C50 diol or polyol, aliphatic esters of an ester resulting from the esterification of an aliphatic hydroxycarboxylic acid ester with an aliphatic carboxylic acid, and a mixture thereof. Non-limiting examples of glyceryl esters include glyceryl behenate, glyceryl erucate, glyceryl hydroxystearate, glyceryl isostearate, glyceryl lanolate, glyceryl laurate, glyceryl linoleate, glyceryl myristate, glyceryl oleate, glyceryl stearate, glyceryl stearate citrate, glyceryl distearate, glyceryl laurate, or a mixture thereof. In at least one instance the glyceryl ester comprises glyceryl stearate, bis-diglyceryl polyacyladipate, or a mixture thereof. In at least one other instance, the glyceryl ester comprises glyceryl stearate.

In general, the amount of the one or more of a second emulsifier(s) chosen from glyceryl ester having a HLB of about 3 to about 6 may range from about 0.5 wt. % to about 5 wt. %, based on the total weight of the composition. In various embodiments, the amount of the one or more of a second emulsifier chosen from glyceryl ester having a HLB of about 3 to about 6 may range from about 0.2 to about 5 wt. %, about 0.2 to about 4 wt. %, about 0.2 to about 3 wt. %, about 0.5 wt. % to about 4 wt. %, about 0.5 to about 3 wt. %, about 0.5 to about 2 wt. %, about 0.6 to about 5 wt. %, about 0.6 to about 4 wt. %, about 0.6 to about 3 wt. %, about 0.6 to about 2 wt. %, about 0.8 to about 4 wt. %, about 0.8 wt. % about 3 wt. %, or about 0.8 to about 2 wt. %, about 1.0 to about 4 wt. %, about 1.0 wt. % about 3 wt. %, or about 1.0 to about 2 wt. %, based on the total weight of the composition.

(e) Ethoxylated Fatty Acids

The composition of the instant disclosure includes one or more third emulsifier(s) chosen from ethoxylated fatty acids. "Ethoxylated fatty acids" are also known as "ethoxylated fatty acid esters" and polyethoxylated fatty acids." They are formed when a fatty acid is reacted with an alkylene oxide. The resulting product may be a monoester, diester, or mixture thereof.

The ethoxylated fatty acids can be represented by the formula R—C(O)O(CH$_2$CH$_2$O)$_n$—H, wherein R represents the aliphatic residue of a fatty acid and n represents the number of molecules of ethylene oxide. In another aspect, n is an integer ranging from 2 to 200, 2 to 150, 2 to 100, 2 to 50, 3 to 200, 3 to 150, 3 to 100, 3 to 50, or 3 to 25 in another aspect, and 3 to 10 in a further aspect. In still another aspect of the invention, R is derived from a fatty acid containing 8 to 24 carbon atoms. Exemplary ethoxylated fatty acids include but are not limited to capric acid ethoxylate, lauric acid ethoxylate, myristic acid ethoxylate, stearic acid ethoxylate, oleic acid ethoxylate, coconut fatty acid ethoxylate, and polyethylene glycol 400 propoxylated monolaurate, wherein the number of ethylene oxide units in each of the foregoing ethoxylates can range from 2 and above in one aspect, and from 2 to about 200 in another aspect, from 2 to 200, 2 to 150, 2 to 100, 2 to 50, 3 to 200, 3 to 150, 3 to 100, 3 to 50, or 3 to 25. More specific examples of ethoxylated fatty acids are PEG-8 distearate (the 8 meaning the number of repeating ethylene oxide units), PEG-8 behenate, PEG-8 caprate, PEG-8 caprylate, PEG-8 caprylate/caprate, PEG cocoates (PEG without a number designation meaning that the number of ethylene oxide units ranges from 2 to 50), PEG-15 dicocoate, PEG-2 diisononanoate, PEG-8 diisostearate, PEG-dilaurates, PEG-dioleates PEG-distearates, PEG Ditallates, PEG-isostearates, PEG-jojoba acids, PEG-laurates, PEG-linolenates, PEG-myristates, PEG-oleates, PEG-palmitates, PEG-ricinoleates, PEG-stearates, PEG-tallates, and the like.

Examples of ethoxylated fatty acids that may be mentioned include the adducts of ethylene oxide with esters of lauric acid, palmitic acid, stearic acid or behenic acid, and mixtures thereof, especially those containing from 9 to 100 oxyethylene groups, such as PEG-9 to PEG-50 laurate (as the CTFA names: PEG-9 laurate to PEG-50 laurate); PEG-9 to PEG-50 palmitate (as the CTFA names: PEG-9 palmitate to PEG-50 palmitate); PEG-9 to PEG-50 stearate (as the CTFA names: PEG-9 stearate to PEG-50 stearate); PEG-9 to PEG-50 palmitostearate; PEG-9 to PEG-50 behenate (as the CTFA names: PEG-9 behenate to PEG-50 behenate); polyethylene glycol 100 EO monostearate (CTFA name: PEG-100 stearate); and mixtures thereof.

In some instance, the one or more ethoxylated fatty acids is chosen from polethoxylated stearic acid esters, for example, PEG-9 stearate, PEG-8 distearate, PEG-20 stearate, PEG-8 stearate, PEG-8 oleate, PEG-20 stearate, PEG-30 stearate, PEG-40 stearate, PEG-50 stearate, PEG-100 stearate, PEG-150 laurate, and combinations therefore.

The amount of the one or more third emulsifiers chosen from ethoxylated fatty acids will vary. Nonetheless, in various embodiment is from about 0.5 wt. % to about 5 wt. %, based on the total weight of the composition. In various embodiments, the total amount of the one or more third emulsifiers chosen from ethoxylated fatty acids is from about 0.2 to about 5 wt. %, about 0.2 to about 4 wt. %, about 0.2 to about 3 wt. %, about 0.5 wt. % to about 4 wt. %, about 0.5 to about 3 wt. %, about 0.5 to about 2 wt. %, about 0.6 to about 5 wt. %, about 0.6 to about 4 wt. %, about 0.6 to about 3 wt. %, about 0.6 to about 2 wt. %, about 0.8 to about 4 wt. %, about 0.8 to about 3 wt. %, or about 0.8 to about 2 wt. %, about 1.0 to about 4 wt. %, about 1.0 to about 3 wt. %, or about 1.0 to about 2 wt. %, based on the total weight of the composition.

(f) Fatty Alcohols

The term "fatty alcohol" means an alcohol comprising at least one hydroxyl group (OH), and comprising at least 8 carbon atoms, and which is neither oxyalkylenated (in particular neither oxyethylenated nor oxypropylenated) nor glycerolated. The fatty alcohols can be represented by: R—OH, wherein R denotes a saturated (alkyl) or unsaturated (alkenyl) group, linear or branched, comprising from 8 to 40 carbon atoms, preferably 10 to 30 carbon atoms, more preferably 12 to 24 carbon atoms, and even more preferably 14 to 22 carbon atoms.

The fatty alcohol(s) may be liquid or solid. In some instances, it is preferable that the cosmetic compositions include at least one solid fatty alcohol. The solid fatty alcohols that can be used include those that are solid at ambient temperature and at atmospheric pressure (25° C., 780 mmHg), and are insoluble in water, that is to say they have a water solubility of less than 1% by weight, preferably less than 0.5% by weight, at 25° C., 1 atm.

The solid fatty alcohols may be represented by: R—OH, wherein R denotes a linear alkyl group, optionally substituted with one or more hydroxyl groups, comprising from 8 to 40 carbon atoms, preferably 10 to 30 carbon atoms, more preferably 12 to 24 carbon atoms, and even more preferably 14 to 22 carbon atoms.

Non-limiting examples of useful fatty alcohols include lauryl alcohol or lauryl alcohol (1-dodecanol); myristic or myristyl alcohol (1-tetradecanol); cetyl alcohol (1-hexadecanol); stearyl alcohol (1-octadecanol); arachidyl alcohol (1-eicosanol); behenyl alcohol (1-docosanol); lignoceryl alcohol (1-tetracosanol); ceryl alcohol (1-hexacosanol); montanyl alcohol (1-octacosanol); myricylic alcohol (1-triacontanol), and mixtures thereof.

In certain embodiments, the one or more fatty alcohols have from 12 to 24 carbon atoms. Specific nonlimiting examples include cetyl alcohol, stearyl alcohol, cetearyl alcohol, behenyl alcohol, lauryl alcohol, myristic or myristyl alcohol, arachidyl alcohol, lignoceryl alcohol, or mixtures thereof.

Preferably, the cosmetic composition includes one or more solid fatty alcohol, for example, chosen from cetyl alcohol, stearyl alcohol, behenyl alcohol and mixtures thereof such as cetylstearyl or cetearyl alcohol.

The liquid fatty alcohols, in particular those containing C10-C34, preferably have branched carbon chains and/or have one or more, preferably 1 to 3 double bonds. They are preferably branched and/or unsaturated (C═C double bond) and contain from 12 to 40 carbon atoms.

The liquid fatty alcohols may be represented by: R—OH, wherein R denotes a C12-C24 branched alkyl group or an alkenyl group (comprising at least one C12-C24 double bond C═C), R being optionally substituted by a or more hydroxy groups. Preferably, the liquid fatty alcohol is a branched saturated alcohol. Preferably, R does not contain a hydroxyl group. These include oleic alcohol, linoleic alcohol, linolenic alcohol, isocetyl alcohol, isostearyl alcohol, 2-octyl-1-dodecanol, 2-butyloctanol, 2-hexyl-1-decanol, 2-decyl-1-tetradecanol, 2-tetradecyl-1-cetanol and mixtures thereof. Preferably, the liquid fatty alcohol is 2-octyl-1-dodecanol.

In some instances, the cosmetic compositions include one or more fatty alcohols selected from decyl alcohol, undecyl alcohol, dodecyl, myristyl, cetyl alcohol, stearyl alcohol, cetearyl alcohol, isostearyl alcohol, isocetyl alcohol, behenyl alcohol, linalool, oleyl alcohol, myricyl alcohol and a mixture thereof. In some instances, the cosmetic compositions preferably include stearyl alcohol.

The amount of one or more fatty alcohols in the cosmetic compositions may vary but in various embodiments ranges from about 0.2 wt. % to about 5 wt. %, based on the total weight of the composition. In various embodiments, the amount of the one or more fatty alcohols in the composition ranges from about 0.2 to about 5 wt. %, about 0.2 to about 4 wt. %, about 0.2 to about 3 wt. %, about 0.2 to about 2 wt. %, about 0.3 to about 5 wt. %, about 0.3 to about 4 wt. %, about 0.3 to about 3 wt. %, about 0.3 to about 2 wt. %, about 0.5 to about 4 wt. %, about 0.5 to about 3 wt. %, about 0.5 to about 2 wt. %, about 0.7 to about 4 wt. %, about 0.7 to about 3 wt. %, about 0.7 to about 2 wt. %, based on the total weight of the composition.

(g) Non-Triglyceride and Non-Aromatic Fatty Compounds

The cosmetic composition of the instant disclosure includes one or more non-triglyceride and non-aromatic fatty compounds. The non-triglyceride and non-aromatic fatty compounds are different from the ethoxylated fatty acids (e) and the fatty alcohols (f). Also, as the name indicates, they are not triglycerides or aromatic fatty compounds. The term "fatty compounds" is interchangeable with the "fatty materials." Fatty compounds are known as compounds that are not soluble (or only sparingly soluble) in water; they are hydrophilic and are often solubilized in organic solvents. They include materials such as oils, fats, waxes, hydrocarbons, fatty esters, etc. For purposes of the instant disclosure, "fatty compounds" do not include glycerides, aromatic fatty compounds, ethoxylated fatty acids, and fatty alcohols, as indicated above. In addition, silicones are not considered fatty compounds according to the instant disclosure. In certain embodiments, nonlimiting examples of non-triglyceride and non-aromatic fatty compounds include oils, waxes, alkanes (paraffins), fatty acids, fatty esters, lanolin, hydrocarbons, derivatives thereof, and mixtures thereof. Fatty compounds are described by the International Federation Societies of Cosmetic Chemists, for example, in Cosmetic Raw Material Analysis and Quality, *Volume I: Hydrocarbons, Glycerides, Waxes and Other Esters* (Redwood Books, 1994), which is incorporated herein by reference in its entirety.

Non-limiting examples of non-triglyceride and non-aromatic fatty compounds include fatty esters (isopropyl myristate, sorbitan isostearate), sarcosinates, for instance an acyl sarcosinate, plant and/or vegetable oils, and mixtures thereof. Non-limiting examples of sarcosinates include sodium lauroyl sarcosinate, sodium cocoyl sarcosinate, sodium myristoyl sarcosinate, sodium caproyl sarcosinate, TEA-cocoyl sarcosinate, ammonium cocoyl sarcosinate, ammonium lauroyl sarcosinate, dimer dilinoleyl bis-lauroyl-glutamate/lauroylsarcosinate, disodium lauroamphodiacetate lauroyl sarcosinate, isopropyl lauroyl sarcosinate, potassium cocoyl sarcosinate, potassium lauroyl sarcosinate, sodium cocoyl sarcosinate, sodium lauroyl sarcosinate, sodium myristoyl sarcosinate, sodium oleoyl sarcosinate, sodium palmitoyl sarcosinate, TEA-cocoyl sarcosinate, TEA-lauroyl sarcosinate, TEA-oleoyl sarcosinate, TEA-palm kernel sarcosinate, and combinations thereof.

In one embodiment, it is preferably that the one or more one or more non-triglyceride and non-aromatic fatty compounds are chosen from fatty esters (e.g., isopropyl myristate, sorbitan isostearate), acyl sarcosinates (e.g., isopropyl lauroyl sarcosinate), and mixtures thereof.

Nonlimiting examples of non-triglyceride and non-aromatic fatty compounds include oils, mineral oil, alkanes (paraffins), fatty acids, fatty alcohol derivatives, fatty acid derivatives, esters of fatty alcohols, hydroxy-substituted fatty acids, waxes, lanolin, and a mixture thereof.

Fatty Alcohol Derivatives

Fatty alcohol derivatives include fatty esters derived from one or more fatty alcohols. Fatty alcohol derivatives also include alkoxylated fatty alcohols, e.g., having about 1 to about 100 moles of an alkylene oxide per mole of alkoxylated fatty alcohol. For example, the alkoxylated fatty alcohols may be alkoxylated with about 1 to about 80 moles, about 2 to about 50, about 5 to about 45 moles, about 10 to about 40 moles, or 15 to about 35 mores, including all ranges and subranges therebetween, of an alkylene oxide per mole of alkoxylated fatty alcohol.

As examples of alkoxylated fatty alcohols, steareth (for example, steareth-2, steareth-20, and steareth-21), laureth (for example, laureth-4, and laureth-12), ceteth (for example, ceteth-10 and ceteth-20) and ceteareth (for example, ceteareth-2, ceteareth-10, and ceteareth-20) are mentioned. In at least one instance, the one or more alkoxylated fatty alcohols include steareth-20. In some instances, the one or more alkoxylated fatty alcohols may be exclusively steareth-20.

Additional fatty alcohol derivatives that may, optionally be suitable include methyl stearyl ether; 2-ethylhexyl dodecyl ether; stearyl acetate; cetyl propionate; the ceteth series of compounds, such as ceteth-1 through ceteth-45, which are ethylene glycol ethers of cetyl alcochol, wherein the numeric designation indicates the number of ethylene glycol moieties present; the steareth series of compounds such as steareth-1 through 10, which are ethylene glycol ethers of steareth alcohol, wherein the numeric designation indicates the number of ethylene glycol moieties present; ceteareth 1 through ceteareth-10, which are the ethylene glycol ethers of ceteareth alcohol, i.e. a mixture of fatty alcohols containing predominantly cetyl and stearyl alcohol, wherein the numeric designation indicates the number of ethylene glycol moieties present; C1-C30 alkyl ethers of the ceteth, steareth, and ceteareth compounds just described; polyoxyethylene ethers of branched alcohols such as octyldodecyl alcohol, dodecylpentadecyl alcohol, hexyldecyl alcohol, and isostearyl alcohol; polyoxyethylene ethers of behenyl alcohol; PPG ethers such as PPG-9-steareth-3, PPG-11 stearyl ether, PPG8-ceteth-1, and PPG-10 cetyl ether; and a mixture thereof.

Fatty Acids and Fatty Acid Derivatives

The fatty acids may be straight or branched chain acids and/or may be saturated or unsaturated. Non-limiting examples of fatty acids include diacids, triacids, and other multiple acids as well as salts of these fatty acids. For example, the fatty acid may optionally include or be chosen from lauric acid, palmitic acid, stearic acid, behenic acid, arichidonic acid, oleic acid, isostearic acid, sebacic acid, and a mixture thereof. In some cases, the fatty acids are selected from the group consisting of palmitic acid, stearic acid, and a mixture thereof.

Fatty acid derivatives are not polyglycerol esters of fatty acids (c) but include, for example, fatty acid esters of the fatty alcohols, fatty acid esters of the fatty alcohol derivatives, fatty acid esters of alcohols, hydroxy-substituted fatty acids, and a mixture thereof. Non-limiting examples of fatty acid derivatives include ricinoleic acid, glycerol monostearate, 12-hydroxy stearic acid, ethyl stearate, cetyl stearate, cetyl palmitate, polyoxyethylene cetyl ether stearate, polyoxyethylene stearyl ether stearate, polyoxyethylene lauryl ether stearate, ethyleneglycol monostearate, propyleneglycol monostearate, propyleneglycol distearate, trimethylolpropane distearate, sorbitan stearate, dimethyl sebacate, PEG-15 cocoate, PPG-15 stearate, glyceryl monostearate, glyceryl distearate, glyceryl tristearate, and a mixture thereof.

Waxes

Non-limiting examples of waxes in this category include for example, synthetic wax, ceresin, paraffin, ozokerite, polyethylene waxes, illipe butter, beeswax, carnauba, microcrystalline, lanolin, lanolin derivatives, candelilla, cocoa butter, shellac wax, spermaceti, bran wax, capok wax, sugar cane wax, montan wax, whale wax, bayberry wax, acacia decurrents flower wax, vegetable waxes (such as sunflower seed (*Helianthus annuus*), carnauba, candelilla, ouricury or japan wax or cork fibre or sugarcane waxes), or a mixture thereof.

Oils

Suitable oils include, but are not limited to, natural oils, such as coconut oil; hydrocarbons, such as mineral oil and hydrogenated polyisobutene; fatty alcohols, such as octyldodecanol; esters, such as $C_{12}$-$C_{15}$ alkyl benzoate; diesters, such as propylene dipelarganate; and triesters, such as glyceryl trioctanoate. Non-limiting examples of oils that may, optionally, be included in the cosmetic compositions include isotridecyl isononanoate, PEG-4 diheptanoate, isostearyl neopentanoate, tridecyl neopentanoate, cetyl octanoate, cetyl palmitate, cetyl ricinoleate, cetyl stearate, cetyl myristate, coco-dicaprylate/caprate, decyl isostearate, isodecyl oleate, isodecyl neopentanoate, isohexyl neopentanoate, octyl palmitate, dioctyl malate, tridecyl octanoate, myristyl myristate, octododecanol, or combinations of octyldodecanol, acetylated lanolin alcohol, cetyl acetate, isodocecanol, polyglyceryl-3-diisostearate, castor oil, lanolin and lanolin derivatives, triisocetyl citrate, sorbitan sesquioleate, coconut oil, corn oil, cottonseed oil, glyceryl triacetyl hydroxystearate, glyceryl triacetyl ricinoleate, glyceryl trioctanoate, hydrogenated castor oil, linseed oil, mink oil, olive oil, palm oil, illipe butter, rapeseed oil, soybean oil, sunflower seed oil, tallow, tricaprin, trihydroxystearin, triisostearin, trilaurin, trilinolein, trimyristin, triolein, tripalmitin, tristearin, walnut oil, wheat germ oil, cholesterol, or combinations thereof.

Acyl Sarcosinates

Non-limiting examples of acyl sarcosinates include sodium lauroyl sarcosinate, sodium cocoyl sarcosinate, sodium myristoyl sarcosinate, sodium caproyl sarcosinate, TEA-cocoyl sarcosinate, ammonium cocoyl sarcosinate, ammonium lauroyl sarcosinate, dimer dilinoleyl bis-lauroyl-glutamate/lauroylsarcosinate, disodium lauroamphodiacetate lauroyl sarcosinate, isopropyl lauroyl sarcosinate, potassium cocoyl sarcosinate, potassium lauroyl sarcosinate, sodium cocoyl sarcosinate, sodium lauroyl sarcosinate, sodium myristoyl sarcosinate, sodium oleoyl sarcosinate, sodium palmitoyl sarcosinate, TEA-cocoyl sarcosinate, TEA-lauroyl sarcosinate, TEA-oleoyl sarcosinate, TEA-palm kernel sarcosinate, and combinations thereof.

In a preferred embodiment, the one or more non-triglyceride and non-aromatic fatty compounds are chosen from fatty esters (e.g., isopropyl myristate, sorbitan isostearate), acyl sarcosinates (e.g., isopropyl lauroyl sarcosinate), and mixtures thereof.

The total amount of the one or more non-triglyceride and non-aromatic fatty compounds will vary. Nonetheless, in certain embodiments the total amount of the non-triglyceride and non-aromatic fatty compounds is from about 4 to about 20 wt. %, based on the total weight of the composition. In further embodiments, total amount of the one or more non-triglyceride and non-aromatic fatty compounds is from about 1 to about 20 wt. %, about 1 to about 15 wt. %, about 1 to about 10 wt. %, about 2 to about 20 wt. %, about 2 to about 15 wt. %, about 2 to about 10 wt. %, about 3 to about 20 wt. %, about 3 to about 15 wt. %, about 3 to about 10 wt. %, about 4 to about 20 wt. %, about 4 to about 15 wt. %, or about 4 to about 10 wt. %, based on the total weight of the composition.

(h) Hydroxypropyl Tetrahydropyrantriol

The cosmetic compositions of the instant disclosure do not require, nor do they necessarily include hydroxypropyl tetrapyrantriol—it is optional. Nonetheless, in various embodiments it is preferably to include hydroxypropyl tetrapyrantriol. Hydroxypropyl tetrapyrantriol is a sugar-protein hybrid made from xylose and can effectively activate the synthesis of GAGs (glycosamineoglycans), promote the production of hyaluronic acid, synthesis of collagen, adhesion between the dermis and the epidermis, the synthesis of epidermal structural components, the regeneration of damaged tissue, and maintain skin elasticity.

The amount of hydroxypropyl tetrapyrantriol in the composition, if present, will vary. Nonetheless, in various embodiments, the total amount of hydroxypropyl tetrapyrantriol is from about 10 wt. % to about 40 wt. % based on the total weight of the composition. In further embodiments, the total amount of the hydroxypropyl tetrapyrantriol in the composition is from about 10 wt. % to about 35 wt. %, from about 10 to about 30 wt. %, from about 10 to about 25 wt. %, from about 10 to about 20 wt. %, about 12 to about 35 wt. %, about 12 to about 30 wt. %, about 12 to about 25 wt. %, about 12 to about 20 wt. %, from about 12 to about 18 wt. %, from about 14 to about 30 wt. %, from about 14 to about 25 wt. %, from about 14 to about 20 wt. %, or from about 14 to about 18 wt. %, based on the total weight of the composition.

(i) Thickening Polymers

In various embodiments, the cosmetic compositions of the instant disclosure may optionally include one more thickening polymer(s). Non-limiting examples of various types of thickening polymers include polyacrylate, polymethacrylate, polyethylacrylate, and polyacrylamide, acrylic acid/acrylonitrogens copolymer, hydroxyethyl acrylate/sodium acryloyldimethyl taurate copolymer, acrylates/steareth-20 itaconate copolymer, acrylates/ceteth-20 itaconate copolymer, Acrylates/Aminoacrylates/C10-30 Alkyl PEG-20 Itaconate Copolymer, acrylates/aminoacrylates copolymer, acrylates/steareth-20 methacrylate copolymer, acrylates/beheneth-25 methacrylate copolymer, acrylates/steareth-20 methacrylate crosspolymer, acrylates/beheneth-25 methacrylate/HEMA crosspolymer, acrylates/vinyl neodecanoate crosspolymer, acrylates/vinyl isodecanoate crosspolymer, Acrylates/Palmeth-25 Acrylate Copolymer, Acrylic Acid/Acrylamidomethyl Propane Sulfonic Acid Copolymer, and acrylates/C10-C30 alkyl acrylate crosspolymer, carbomers, hydrophobically modified polypolyacrylates; hydrophobically modified polyacrylic acids, hydrophobically modified polyacrylamides; hydrophobically modified polyethers wherein these materials may have a hydrophobe that can be selected from cetyl, stearyl, oleayl, and combinations thereof, acrylamide/ammonium acrylate copolymer; acrylamide/sodium acryloyldimethyl taurate copolymer/isohexadecane/polysorbate 80, ammonium acryloyldimethyltaurate/VP copolymer, Sodium Acrylate/Sodium Acryloyldimethyl Tau rate Copolymer, acrylates copolymer, Acrylates Crosspolymer-4, Acrylates Crosspolymer-3, acrylates/beheneth-25 methacrylate copolymer, acrylates/C10-C30 alkyl acrylate crosspolymer, acrylates/steareth-20 itaconate copolymer, ammonium polyacrylate/Isohexadecane/PEG-40 castor oil; sodium carbomer, crosslinked polyvinylpyrrolidone (PVP), polyacrylamide/C13-14 isoparaffin/laureth-7, polyacrylate 13/polyisobutene/polysorbate 20, polyacrylate crosspolymer-6, polyamide-3, polyquaternium-37, Acrylamide/Sodium Acryloyldimethyltaurate/Acrylic Acid Copolymer, sodium acrylate/acryloyldimethyltaurate, sodium polyacrylate, and a mixture thereof.

Among the nonionic thickening polymers that may be mentioned are:
(1) Celluloses modified with groups comprising at least one fatty chain; examples that may be mentioned include: hydroxyethylcelluloses modified with groups comprising at least one fatty chain, such as alkyl, arylalkyl or alkylaryl groups, or mixtures thereof, and in which the alkyl groups are preferably C8-C22, for instance the product NATROSOL PLUS GRADE 330 CS ($C_{16}$ alkyls) sold by the company Aqualon, or the product BERMOCOLL EHM 100 sold by the company Berol Nobel; and hydroxyethylcelluloses modified with alkylphenyl polyalkylene glycol ether groups, such as the product AMERCELL POLYMER HM-1500 (polyethylene glycol (15) nonylphenyl ether) sold by the company Amerchol,
(2) Hydroxypropyl guars modified with groups comprising at least one fatty chain, such as the product ESA-FLOR HM 22 ($C_{22}$ alkyl chain) sold by the company Lamberti, and the products RE210-18 ($C_{14}$ alkyl chain) and RE205-1 ($C_{20}$ alkyl chain) sold by the company Rhone-Poulenc,
(3) Copolymers of vinylpyrrolidone and of fatty-chain hydrophobic monomers; examples that may be mentioned include: the products ANTARON V216 or GANEX V216 (vinylpyrrolidone/hexadecene copolymer) sold by the company I.S.P. the products ANTARON V220 or GANEX V220 (vinylpyrrolidone/eicosene copolymer) sold by the company I.S.P.,
(4) Copolymers of $C_1$-$C_6$ alkyl methacrylates or acrylates and of amphiphilic monomers comprising at least one fatty chain, for instance the oxyethylenated methyl acrylate/stearyl acrylate copolymer sold by the company Goldschmidt under the name ANTIL 208,
(5) Copolymers of hydrophilic methacrylates or acrylates and of hydrophobic monomers comprising at least one fatty chain, for instance the polyethylene glycol methacrylate/lauryl methacrylate copolymer,
(6) Polyurethane polyethers comprising in their chain both hydrophilic blocks usually of polyoxyethylenated nature and hydrophobic blocks, which may be aliphatic sequences alone and/or cycloaliphatic and/or aromatic sequences.

In a particularly preferred embodiment, the one or more thickening polymers is chosen from polyacrylates (e.g., sodium polyacrylate), hydroxyethyl acrylate/sodium acryloyldimethyl taurate copolymer, ammonium acryloyldimethyltaurate/VP copolymer, acrylamide/sodium acryloyldimethyltaurate copolymer, polyacrylate crosspolymer-6, polyacrylamide, acrylatesc10-30 alkyl acrylate crosspolymer and mixtures thereof.

The amount of the one or more thickening polymers, when present, will vary. Nonetheless, in various embodiments the total amount of the one or more thickening polymers is from about 0.01 to about 5 wt. %, based on the total weight of the composition. In further embodiments, the total amount of the one or more thickening polymers is from about 0.01 to about 4 wt. %, about 0.01 to about 3 wt. %, about 0.1 to about 5 wt. %, about 0.1 to about 4 wt. %, about 0.1 to about 3 wt. %, about 0.5 to about 5 wt. %, about 0.5 to about 4 wt. %, or about 0.5 to about 3 wt. %, about 1 to about 5 wt. %, about 1 to about 4 wt. %, or about 1 to about 3 wt. %, about 1.5 to about 5 wt. %, about 1.5 to about 4 wt. %, or about 1.5 to about 3 wt. %, based on the total weight of the composition.

(j) Water-Soluble Solvents

The term "water-soluble solvent" is interchangeable with the term "water-miscible solvent" and means a compound that is liquid at 25° C. and at atmospheric pressure (760 mmHg), and it has a solubility of at least 50% in water under these conditions. In some cases, the water-soluble solvents have a solubility of at least 60%, 70%, 80%, or 90%. Non-limiting examples of water-soluble solvents include, for example, glycerin, alcohols (for example $C_{1-10}$ or $C_{1-4}$ alcohols), organic solvents, polyols, glycols, and a mixture thereof.

As examples of organic solvents, non-limiting mentions can be made of monoalcohols and polyols such as ethyl alcohol, isopropyl alcohol, propyl alcohol, isopropyl alcohol, benzyl alcohol, 4-tert-butylcyclohexanol, and phenylethyl alcohol, or glycols or glycol ethers such as, for example, monomethyl, monoethyl and monobutyl ethers of ethylene glycol, propylene glycol or ethers thereof such as, for example, monomethyl ether of propylene glycol, butylene glycol, hexylene glycol, dipropylene glycol as well as alkyl ethers of diethylene glycol, for example monoethyl ether or monobutyl ether of diethylene glycol. Other suitable examples of organic solvents are ethylene glycol, propylene glycol, butylene glycol, hexylene glycol, propane diol, and glycerin. The organic solvents can be volatile or non-volatile compounds.

Further non-limiting examples of water-soluble solvents include alkanediols (polyhydric alcohols) such as glycerin, 1,2,6-hexanetriol, trimethylolpropane, ethylene glycol, propylene glycol, diethylene glycol, triethylene glycol, tetraethylene glycol, pentaethylene glycol, dipropylene glycol, 2-butene-1,4-diol, 2-ethyl-1,3-hexanediol, 2-methyl-2,4-pentanediol, (caprylyl glycol), 1,2-hexanediol, 1,2-pentanediol, and 4-methyl-1,2-pentanediol; alkyl alcohols having 1 to 4 carbon atoms such as ethanol, methanol, butanol, propanol, and isopropanol; glycol ethers such as ethylene glycol monomethyl ether, ethylene glycol monoethyl ether, ethylene glycol monobutyl ether, ethylene glycol monomethyl ether acetate, diethylene glycol monomethyl ether, diethylene glycol monoethyl ether, diethylene glycol mono-n-propyl ether, ethylene glycol mono-iso-propyl ether, diethylene glycol mono-iso-propyl ether, ethylene glycol mono-n-butyl ether, ethylene glycol mono-t-butyl ether, diethylene glycol mono-t-butyl ether, 1-methyl-1-methoxybutanol, propylene glycol monomethyl ether, propylene glycol monoethyl ether, propylene glycol mono-t-butyl ether, propylene glycol mono-n-propyl ether, propylene glycol mono-iso-propyl ether, dipropylene glycol monomethyl ether, dipropylene glycol monoethyl ether, dipropylene glycol mono-n-propyl ether, and dipropylene glycol mono-iso-propyl ether; 2-pyrrolidone, N-methyl-2-pyrrolidone, 1,3-dimethyl-2-imidazolidinone, formamide, acetamide, dimethyl sulfoxide, sorbit, sorbitan, acetine, diacetine, triacetine, sulfolane, and a mixture thereof.

Polyhydric alcohols are also useful. Examples of polyhydric alcohols include glycerin, ethylene glycol, diethylene glycol, triethylene glycol, propylene glycol, dipropylene glycol, tripropylene glycol, 1,3-butanediol, 2,3-butanediol, 1,4-butanediol, 3-methyl-1,3-butanediol, 1,5-pentanediol, tetraethylene glycol, 1,6-hexanediol, 2-methyl-2,4-pentanediol, polyethylene glycol, 1,2,4-butanetriol, 1,2,6-hexanetriol, and a mixture thereof. Polyol compounds may also be used. Non-limiting examples include the aliphatic diols, such as 2-ethyl-2-methyl-1,3-propanediol, 3,3-dimethyl-1,2-butanediol, 2,2-diethyl-1,3-propanediol, 2-methyl-2-propyl-1,3-propanediol, 2,4-dimethyl-2,4-pentanediol, 2,5-dimethyl-2,5-hexanediol, 5-hexene-1,2-diol, and 2-ethyl-1,3-hexanediol, and a mixture thereof.

In some instances, the cosmetic compositions of the instant disclosure include one or more glycols and/or one or more alcohols, for example, one or more water-soluble solvents selected from the group consisting of butylene glycol, capryloyl glycol, propanediol, glycerin, and a mixture thereof.

The total amount of the one or more water-soluble solvents can and will vary but is typically about 1 to about 20 wt. %, based on the total weight of the cosmetic composition. In some cases, the total amount of the one or more water-soluble solvents may be about 1 to about 15 wt. %, about 1 to about 10 wt. %, about 1 to about 5 wt. %, about 2 to about 20 wt. %, about 2 to about 15 wt. %, about 2 to about 10 wt. %, about 2 to about 5 wt. %, about 5 to about 20 wt. %, about 5 to about 15 wt. %, or about 5 to about 10 wt. %, based on the total weight of the cosmetic composition.

Miscellaneous Ingredients

The cosmetic compositions of the instant disclosure may optionally include one or more miscellaneous ingredients. Miscellaneous ingredients are ingredients that are compatible with the cosmetic compositions and do not disrupt or materially affect the basic and novel properties of the cosmetic compositions. Miscellaneous ingredients commonly used in cosmetics are known in the art. Non-limiting examples include miscellaneous emulsifiers/surfactants other than the one or more first emulsifiers chosen from polyglycerol-based emulsifiers of (c), the one or more second emulsifiers chosen from glyceryl esters having an HLB of about 3 to about 6 of (d), and the one or more third emulsifiers chosen from ethoxylated fatty acids of (e), preservatives, fragrances, pH adjusters, salts, buffers, antioxidants, flavonoids, vitamins, botanical extracts, UV filtering agents, proteins, protein hydrolysates and/or isolates, hydrotropes, pearlescent agents, fillers, colorants, mattifying agents, further skin active agents, depigmenting agents, anti-wrinkle agents, etc. Nonlimiting examples of various miscellaneous ingredients that may optionally be include (or excluded) from the cosmetic compositions is provided below.

Miscellaneous Emulsifiers/Surfactants

Miscellaneous emulsifiers/surfactants may optionally be included in the cosmetic compositions. Miscellaneous emulsifiers/surfactants are those other than the one or more first emulsifiers chosen from polyglycerol-based emulsifiers of (c), the one or more second emulsifiers chosen from glyceryl esters having an HLB of about 3 to about 6 of (d), and the one or more third emulsifiers chosen from ethoxylated fatty acids of (e). The miscellaneous emulsifiers/surfactants may be nonionic, anionic, cationic, and/or amphoteric/zwitterionic.

Antioxidants

Examples of antioxidants include tocopherols (e.g. d-α-tocopherol, d-β-tocopherol, d-γ-tocopherol, d-delta-tocopherol), tocotrienols (e.g. d-α-tocotrienol, d-β-tocotrienol, d-γ-tocotrienol, d-delta-tocotrienol,) and vitamin E (α-tocopherol acetate). These compounds may be isolated from natural sources, prepared by synthetic means, or mixtures thereof. Tocotrienol-enriched vitamin E preparations may be obtained by fractionating vitamin E preparations to remove a portion of tocopherols and recover a preparation more highly concentrated in tocotrienol. Useful tocotrienols are natural products isolated, for example, from wheat germ oil, grain, or palm oil using high performance liquid chromatography, or isolated by alcohol extraction and/or molecular distillation from barley, brewer's grain or oats. As used herein, the term "tocotrienols" includes tocotrienol-rich-fractions obtained from these natural products as well as the pure compounds. The increased glutathione peroxidase activity protects the skin from oxidative damage.

Vitamin C and derivatives may be used, including ascorbic acid, sodium ascorbate, and the fat soluble esters tetrahexyldecyl ascorbate and ascorbyl palmitate, magnesium ascorbyl phosphate, ascorbyl-glucoside, glucosamine ascorbate, ascorbyl acetate, etc. Additionally, extracts from plants containing a high amount of vitamin C such as camu berry (*Myrciaria dubia*), acerola, *Emblica officinalis*, and bioflavonoids from rose hip and citrus may be used including water soluble bioflavonoids such as hesperidin methyl chalcone may also be used.

Sesame (*Sesamum indicum*) or sesame lignan may also be added. Sesame and its lignans (the fibrous compounds associated with the sesame) act as antioxidants. Sesame seed lignans significantly enhance vitamin E activity.

In addition, carotenoids, particularly the xanthophyll type, are also useful antioxidants that can be used. The xanthopyll type carotenoids include molecules, such as lutein, canthaxantin, cryptoxanthin, zeaxanthin and astaxanthin. Xanthophylls protect compounds, such as vitamin A, vitamin E, and other carotenoids.

Flavonoids can also function as antioxidants. In some instances, the flavonoid is a flavanone (derivative of 2,3-dihydro-2-phenylchromen-4-one). Flavones include: Butin, Eriodictyol, Hesperetin, Hesperidin, Homoeriodictyol, Isosakuranetin, Naringenin, Naringin, Pinocembrin, Poncirin, Sakuranetin, Sakuranin, and Sterubin. The flavonoid may be a flavanonol (derivative of 3-hydroxy-2,3-dihydro-2-phenylchromen-4-one). Flavanols include: Taxifolin, Aromadedrin, Chrysandroside A, Chrysandroside B, Xeractinol, Astilbin, and Fustin. The flavonoid may be a flavone (derivative of 2-phenylchromen-4-one). Flavones include: Apigenin, Luteolin, Tangeritin, Chrysin, Baicalein, Scutellarein, Wogonin, Synthetic Flavones: Diosmin, and Flavoxate. The flavonoid may be a flavonol (derivative of 3-hydroxy-2-phenylchromen-4-one). Flavonols include: 3-Hydroxyflavone, Azaleatin, Fisetin, Galangin, Gossypetin, Kaempferide, Kaempferol, Isorhamnetin, Morin, Myricetin, Natsudaidain, Pachypodol, Quercetin, Rhamnazin, Rhamnetin, Azalein, Hyperoside, Isoquercitin, Kaempferitrin, Myricitrin, Quercitrin, Robinin, Rutin, Spiraeoside, Xanthorhamnin, Amurensin, Icariin, and Troxerutin. The flavonoid may be a flavan-3-ol (derivatives of 2-phenyl-3,4-dihydro-2H-chromen-3-ol). Flavan-3-ols include: Catechin, Epicatechin, Epigallocatechin, Epicatechin gallate, Epigallocatechin gallate, Epiafzelechin, Fisetinidol, Guibourtinidol, Mesquitol, and Robinetinidol. The flavonoid may be a flavan-4-ol (derivative of 2-phenylchroman-4-ol). Flavan-4-ols include: Apiforol and Luteoforol. The flavonoid may be an isoflavone (derivative of 3-phenylchromen-4-one). Isoflavones include: Genistein, Daidzein, Biochanin A, Formononetin, and the Equol metabolite from Daidzein.

The antioxidant may be an anthocyanidin (derivative of 2-phenylchromenylium cation). Anthocyanidins include: Aurantinidin, Cyanidin, Delphinidin, Europinidin, Luteolinidin, Pelargonidin, Malvidin, Peonidin, Petunidin, Rosinidin, and Xanthone.

The antioxidant may be a Dihydrochalcone (derivative of 1,3-diphenyl-1-propanone). Dihydrochalcones include: Phloretin, Dihydrochalcone phloretin Phlorizin, Aspalathin, Naringin dihydrochalcone, Neohesperidin dihydrochalcone, and Nothofagin. Without limiting the mode of action of the invention, dihydrochalcones may exert an antioxidant effect by reducing reactive free radicals, like reactive oxygen and reactive nitrogen species.

The antioxidant may be an anthocyanin. Anthocyanins and their derivatives are antioxidants. Anthocyanins encompasses a class of flavonoid compounds that are naturally occurring, water-soluble compounds, responsible for the red, purple, and blue colors of many fruits, vegetables, cereal grains, and flowers. Additionally, anthocyanins are collagenase inhibitors. The inhibition of collagenase helps in the prevention and reduction of wrinkles, increase in skin elasticity, etc., which are caused by a reduction in skin collagen. The anthocyanins may be obtained from any portion of various plant sources, such as the fruit, flower, stem, leaves, root, bark, or seeds. One of skill in the art will understand that certain portions of the plant may contain higher natural levels of anthocyanins, and, therefore, those portions are used to obtain the desired anthocyanins. In some instances, antioxidants may include one or more betacyanin. Betacyanins, like anthocyanins, may be obtained from natural sources and are antioxidants.

The antioxidant may be a Phenylpropanoid (derivatives of cinnamic acid). Phenylpropanoids include: Cinnamic acid, Caffeic acid, Ferulic acid, Trans-ferulic acid (including its antioxidant pharmacore 2,6-dihydroxyacetophenome), 5-Hydroxyferulic acid, Sinapic acid, Coumaryl alcohol, Coniferyl alcohol, Sinapyl alcohol, Eugenol, Chavicol, Safrole, P-coumaric acid, and Sinapinic acid. Without limiting the mode of action of the invention, Phenylpropanoids may neutralize free radicals.

The antioxidant may be a Chalcone (derivative of 1,3-diphenyl-2-propen-1-one). Chalcones include: Butein, Okanin, Carthamin, Marein, Sophoradin, Xanthohumol, Flavokvain A, Flavokavain B, Flavokavin C, and synthetic Safalcone.

The antioxidant may be a Curcuminoid. Curcuminoids include: Curcumin, Desmethoxycurcumin, bis-Desmethoxycurcumin, Tetrahydrocurcumin, and Tetrahydrocurcuminoids. Curcumin and tetrahydrocurcuminoids may be derived from rhizomes of *Curcuma longa*. Tetrahydrocurcumin, a metabolite of curcumin, has been found to be a more potent antioxidant and more stable compared to curcumin.

The antioxidant may be a Tannin. Tannins include: Tannin, Terflavin B, Glucogallin, Dgallic acid, and Quercitannic acid.

The antioxidant may be a stilbenoid. Stilbenoids include: Resveratrol, Pterostilbene, and Piceatannol. Resveratrol may include, but is not limited to, 3,5,4'-trihydroxystilbene, 3,4,3',5'-tetrahydroxystilbene (piceatannol), 2,3',4,5'-tetrahydroxystilbene (oxyresveratrol), 4,4'-dihydroxystilbene, and alpha and beta glucoside, galactoside and mannoside derivatives thereof.

The antioxidant may be a Coumarin (derivatives of 2H-chromen-2-one). Coumarins include: 4-Hydroxycoumarin, Umbelliferone, Aesculetin, Herniarin, Auraptene, and Dicoumarol.

The antioxidant may be a Carotenoid. Carotenoids include: beta-Carotene, alpha-Carotene, gamma-Carotene, beta-Cryptoxanthin, Lycopene, Lutein, and Idebenone. Sesame (*Sesamum indicum*) or sesame lignan may also be added. Sesame and its lignans (the fibrous compounds associated with the sesame) act as antioxidants. Sesame seed lignans significantly enhance vitamin E activity.

The antioxidant may be: a Xanthone, Butylated Hydroxytoluene, 2,6-Di-tert-butylphenol, 2,4-Dimethyl-6-tert-butylphenol, Gallic acid, Eugenol, Uric acid, alpha-Lipoic acid, Ellagic acid, Chicoric acid, Chlorogenic acid, Rosmarinic acid, Salicylic acid, Acetylcysteine, S-Allyl cysteine, Barbigerone, Chebulagic acid, Edaravone, Ethoxyquin, Glutathione, Hydroxytyrosol, Idebenone, Melatonin, N-Acetylserotonin, Nordihydroguaiaretic acid, Oleocanthal, Oleuropein, Paradol, Piceatannol, Probucol, Propyl gallate, Protocatechuic acid, Pyritinol, Rutin, Secoisolariciresinol diglucoside, Sesamin, Sesamol, Silibinin, Silymarin, Theaflavin, Theaflavin digallate, Thmoquinone, Trolox, Tyrosol, Polyunsaturated fatty acids, and sulfur-based antioxidants such as Methionine or Lipoic acid.

Skin Active Agents

Nonlimiting examples of skin active agents include retinoic acid, benzoyl peroxide, sulfur, vitamin B6 (pyridoxine or) chloride, selenium, samphire—the cinnamon extract blends, tea and octanoylglycine such as—15 Sepicontrol A5 TEA from Seppic—the mixture of cinnamon, sarcosine and octanoylglycine marketed especially by Seppic under the trade name Sepicontrol A5—zinc salts such as zinc gluconate, zinc pyrrolidonecarboxylate (or zinc pidolate), zinc lactate, zinc aspartate, zinc carboxylate, zinc salicylate 20, zinc cysteate;—derivatives particularly copper and copper pidolate as Cuivridone Solabia—extracts from plants of *Arnica montana*, Cinchona succirubra, Eugenia caryophyllata, *Humulus lupulus, Hypericum perforatum*, Mentha pipenta 25 *Rosmarinus officinalis, Salvia officinalis* and *Thymus vulgaris*, all marketed for example by Maruzen—extracts of meadowsweet (*Spiraea ulmaria*), such as that sold under the name Sebonormine by Silab—extracts of the alga *Laminaria saccharina*, such as that sold under the 30 name Phlorogine by Biotechmarine—the root extracts of burnet mixtures (*Sanguisorba officinalis/Poterium officinale*), rhizomes of ginger (*Zingiber officinalis*) and cinnamon bark (*Cinnamomum cassia*), such as that sold under the name Sebustop by Solabia—extracts of flaxseed such as that sold under the name Linumine by Lucas Meyer—Phellodendron extracts such as those sold under the name Phellodendron extract BG by Maruzen or Oubaku liquid B by Ichimaru Pharcos—of argan oil mixtures extract of *Serenoa serrulata* (saw palmetto) extract and sesame seeds such as that sold under the name Regu SEB by Pentapharm—mixtures of extracts of willowherb, of Terminalia chebula, nasturtium and of bioavailable zinc (microalgae), such as that sold under the name Seborilys Green Tech;—extracts of Pygeum afrianum such as that sold under the name Pygeum afrianum sterolic lipid extract by Euromed—extracts of *Serenoa serrulata* such as those sold under the name Viapure Sabal by Actives International, and those sold by the company Euromed—of extracts of plantain blends, *Berberis aquifolium* and sodium salicylate 20 such as that sold under the name Seboclear Rahn—extract of clove as that sold under the name Clove extract powder by Maruzen—argan oil such as that sold under the name Lipofructyl Laboratories Serobiologiques; 25—lactic protein filtrates, such as that sold under the name Normaseb by Sederma—the seaweed *laminaria* extracts, such as that sold under the name Laminarghane by Biotechmarine—oligosaccharides seaweed *Laminaria digitata*, such as that sold under the name Phycosaccharide 30 AC by the company Codif—extracts of sugar cane such as that sold under the name Policosanol by the company Sabinsa, the sulfonated shale oil, such as that sold under the name Ichtyol Pale by Ichthyol—extracts of meadowsweet (*Spiraea ulmaria*) such as that sold under the name Cytobiol Ulmaire by societeLibiol—sebacic acid, especially sold in the form of a sodium polyacrylate gel under the name Sebosoft by Sederma—glucomannans extracted from konjac tuber and modified with alkylsulfonate chains such as that sold under the name Biopol Beta by Arch Chemical—extracts of *Sophora angustifolia*, such as those sold under the name *Sophora* powder or *Sophora* extract by Bioland—extracts of cinchona bark succirubra such as that sold under the name Red Bark HS by Alban Muller—extracts of *Quillaja saponaria* such as that sold under the name 15 Panama wood HS by Alban Muller—glycine grafted onto an undecylenic chain, such as that sold under the name Lipacide UG OR by SEPPIC—the mixture of oleanolic acid and nordihydroguaiaretic acid, such as that sold under the form of a gel under the name AC.Net by Sederma; 20—phthalimidoperoxyhexanoic acid—citrate tri (C12-C13) sold under the name COSMA-COL.RTM ECI by Sasol; trialkyl citrate (C14-C15) sold under the name COSMACOL.RTM. ECL by Sasol—10-hydroxydecanoic acid, including mixtures acid-hydroxydecanoic October 25, sebacic acid and 1,10-decandiol such as that sold under the name Acnacidol BG by Vincience and mixtures thereof.

Depigmenting Agents

Nonlimiting examples of depigmenting agents include alpha and beta arbutin, ferulic acid, lucinol and its derivatives, kojic acid, resorcinol and derivatives thereof, tranexamic acid and derivatives thereof, gentisic acid, homogentisic, methyl gentisate or homogentisate, dioic acid, D pantheteine calcium sulphonate, lipoic acid, ellagic acid, vitamin B3, linoleic acid and its derivatives, certain compounds derived from plants such as chamomile, bearberry, the aloe family (vera, ferox, bardensis), mulberry, skullcap, a water kiwi fruit (*Actinidia chinensis*) marketed by Gattefosse, an extract of *Paeonia suffruticosa* root, such as that sold by Ichimaru Pharcos under the name Liquid Botanpi Be an extract of brown sugar (*Saccharum officinarum*) such as molasses extract marketed by Taiyo Kagaku under the name Liquid Molasses, without this list being exhaustive. Particular depigmenting agents include alpha and beta arbutin, ferulic acid, kojic acid, resorcinol and derivatives, D pantheteine calcium sulfonate, lipoic acid, ellagic acid, vitamin B3, a water kiwi fruit (*Actinidia chinensis*) marketed by Gattefosse, an extract of *Paeonia suffruticosa* root, such as that sold by the company Ichimaru Pharcos under the name Botanpi Liquid B.

Anti-Wrinkle Agent

The term "anti-wrinkle agent" refers to a natural or synthetic compound producing a biological effect, such as the increased synthesis and/or activity of certain enzymes, when brought into contact with an area of wrinkled skin, this has the effect of reducing the appearance of wrinkles and/or fine lines. Nonlimiting examples of anti-wrinkle agents include: desquamating agents, anti-glycation agents, inhibitors of NO-synthase, agents stimulating the synthesis of dermal or epidermal macromolecules and/or preventing their degradation, agents for stimulating the proliferation of fibroblasts and/or keratinocytes, or for stimulating keratinocyte differentiation reducing agents; muscle relaxants and/or dermo-decontracting agents, anti-free radical agents, and mixtures thereof. Examples of such compounds are: adenosine and its derivatives and retinoids other than retinol (as discussed above, such as retinol palmitate), ascorbic acid and its derivatives such as magnesium ascorbyl phosphate and ascorbyl glucoside; nicotinic acid and its precursors such as nicotinamide; ubiquinone; glutathione and precursors thereof such as L-2-oxothiazolidine-4-carboxylic acid, the compounds C-glycosides and their derivatives as described in particular in EP-1345919, in particular C-beta-D-xylopyranoside-2-hydroxy-propane as described in particular in EP-1345919, plant extracts including sea fennel and extracts of olive leaves, as well as plant and hydrolysates thereof such as rice protein hydrolysates or soybean proteins; algal extracts and in particular *laminaria*, bacterial extracts, the sapogenins such as diosgenin and extracts of *Dioscorea* plants, in particular wild yam, comprising: the α-hydroxy acids, f3-hydroxy acids, such as salicylic acid and n-octanoyl-5-salicylic oligopeptides and pseudodipeptides and acyl derivatives thereof, in particular acid {2-[acetyl-(3-trifluoromethyl-phenyl)-amino]-3-methyl-}acetic acid and lipopeptides marketed by the company under the trade names SEDERMA Matrixyl 500 and Matrixyl 3000; lycopene, manganese salts and magnesium salts, especially gluconates, and mixtures thereof. In at least one case, the skin tightening composition includes adenosine derivatives, such as non-phosphate derivatives of adenosine, such as in particular the 2'-deoxyadenosine, 2',3'-adenosine isopropoylidene; the toyocamycine, 1-methyladenosine, N-6-methyladenosine; adenosine N-oxide, 6-methylmercaptopurine riboside, and the 6-chloropurine riboside. Other derivatives include adenosine receptor agonists such as adenosine phenylisopropyl ("PIA"), 1-methylisoguanosine, N6-cyclohexyladenosine (CHA), N6-cyclopentyladenosine (CPA), 2-chloro-N6-cyclopentyladenosine, 2-chloroadenosine, N6-phenyladenosine, 2-phenylaminoadenosine, MECA, N 6-phenethyladenosine, 2-p-(2-carboxy-ethyl) phenethyl-amino-5'-N-ethylcarboxamido adenosine (CGS-21680), N-ethylcarboxamido-adenosine (NECA), the 5'(N-cyclopropyl)-carboxamidoadenosine, DPMA (PD 129.944) and metrifudil.

The total amount of the one or more miscellaneous ingredients, if present, will vary. Nonetheless, in various embodiments, the total amount of the one or more miscellaneous ingredients, if present, is from about 0.01 to about 10 wt. %, based on the total weight of the cosmetic composition. In further embodiments, the total amount of the one or more miscellaneous ingredients is from about 0.01 to about 8 wt. %, about 0.01 to about 5 wt. %, about 0.01 to about 3 wt. %, about 0.1 to about 10 wt. %, about 0.1 to about 8 wt. %, about 0.1 to about 5 wt. %, about 0.1 to about 3 wt. %, about 1 to about 10 wt. %, about 1 to about 8 wt. %, about 1 to about 5 wt. %, or about 1 to about 3 wt. %, based on the total weight of the cosmetic composition.

As already noted, skin active agents may be included as one or more of the miscellaneous ingredients. With respect to the total amount of skin active agents in the cosmetic compositions, if present, the total amount of skin active agents may be from greater than zero to about 9 wt. %, greater than zero to about 8 wt. %, greater than zero to about 7 wt. %, greater than zero to about 6 wt. %, greater than zero to about 5 wt. %, greater than zero to about 4 wt. %, greater than zero to about 3 wt. %, greater than zero to about 2 wt. %; about 10 ppm to about 10 wt. % (100,000 ppm), about 10 ppm to about 5 wt. % (50,000 ppm), about 10 ppm to about 2.5 wt. % (25,000 ppm), about 10 ppm to about 1 wt. % (10,000 ppm), about 10 ppm to about 0.5 wt. % (5,000 ppm), about 10 ppm to about 0.3 wt. % (3,000 ppm), about 10 ppm to about 0.2 wt. % (2,000 ppm), about 10 ppm to about 0.1 wt. % (1,000 ppm), about 10 ppm to 500 ppm; about 0.1 to about 10 wt. %, about 0.1 to about 5 wt. %, about 0.1 to about 2.5 wt. %, about 0.1 to about 1 wt. %, about 0.1 to about 0.5 wt. %; about 1 to about 10 wt. %, about 1 to about 8 wt. %, about 1 to about 6 wt. %, about 1 to about 5 wt. %, about 1 to about 4 wt. %, about 1 to about 3 wt. %; about 2 to about 10 wt. %, about 2 to about 8 wt.

%, about 2 to about 6 wt. %, about 2 to about 5 wt. %, about 2 to about 4 wt. %; about 3 to about 10 wt. %, about 3 to about 8 wt. %, about 3 to about 6 wt. %, about 3 to about 5 wt. %; about 4 to about 10 wt. %, about 4 to about 8 wt. %, or about 4 to about 6 wt. %, based on the total weight of the cosmetic composition.

pH

In certain embodiments, it is preferable that the cosmetic compositions have a pH of less than 7.0. In further embodiments, the pH of the cosmetic compositions have a pH from about 4.0 to less than 7.0, from about 4.5 to less than 7.0, from about 5.0 to less than 7.0, from about 6.0 to less than 7.0, from about 4.0 to about 6.5, from about 4.5 to about 6.5, from about 5.0 to about 6.5, from about 5.0 to about 6.0. In various embodiments, the pH of the cosmetic compositions does not change by more than ±1 pH unit, ±0.5 pH units, ±0.3 pH units, or ±0.2 pH units, for at least 2 weeks, 4 weeks, and/or 8 weeks in storage at 4° C., 25° C., 37° C., and/or 45° C.

Weight Ratios

In various embodiments, it is preferably that the cosmetic compositions include one or more ratios relating to components (a) and (c)-(g).

In an embodiment, the weight ratio of the one or more first emulsifiers chosen from polyglycerol-based emulsifiers to the ceramide NP is from about 1.5:1 to about 8:1 ((c):(a)), preferably about 1.5:1 to about 5:1, more preferably about 1.5:1 to about 3:1.

In an embodiment, the weight ratio of the one or more second emulsifiers chosen from glyceryl esters having an HLB of about 3 to about 6 to the ceramide NP to is from about 0.8:1 to about 4:1 ((d):(a)), preferably 1:1 to about 3:1, more preferably about 1.2:1 to about 2.5:1.

In an embodiment, the weight ratio of the one or more third emulsifiers chosen from ethoxylated fatty acids to the ceramide NP is from about 0.7:1 to about 4:1 ((e):(a)), preferably about 0.8:1 to about 3:1, more preferably about 0.8:1 to about 2.5:1.

In an embodiment, the weight ratio of the one or more fatty alcohols to the ceramide NP is from about 0.7:1 to about 4:1 ((f):(a)), preferably about 0.8:1 to about 3:1, more preferably about 0.8:1 to about 2.5:1.

In an embodiment, the weight ratio of the one or more non-triglyceride and non-aromatic fatty compounds to the ceramide NP is from about 4:1 to about 20:1 ((g):(a)), preferably about 5:1 to 15:1, more preferably about 6:1 to 10:1.

In a preferred embodiment, the cosmetic compositions include the following ratio relating to components (a) and (c)-(g):

the weight ratio of the one or more first emulsifiers chosen from polyglycerol-based emulsifiers to the ceramide NP is from about 1.5:1 to about 8:1 ((c):(a)), preferably about 1.5:1 to about 5:1, more preferably about 1.5:1 to about 3:1;

the weight ratio of the one or more second emulsifiers chosen from glyceryl esters having an HLB of about 3 to about 6 to the ceramide NP to is from about 0.8:1 to about 4:1 ((d):(a)), preferably 1:1 to about 3:1, more preferably about 1.2:1 to about 2.5:1;

the weight ratio of the one or more third emulsifiers chosen from ethoxylated fatty acids to the ceramide NP is from about 0.7:1 to about 4:1 ((e):(a)), preferably about 0.8:1 to about 3:1, more preferably about 0.8:1 to about 2.5:1;

the weight ratio of the one or more fatty alcohols to the ceramide NP is from about 0.7:1 to about 4:1 ((f):(a)), preferably about 0.8:1 to about 3:1, more preferably about 0.8:1 to about 2.5:1; and the weight ratio of the one or more non-triglyceride and non-aromatic fatty compounds to the ceramide NP is from about 5:1 to about 20:1 ((g):(a)), preferably about 5:1 to 15:1, more preferably about 6:1 to 10:1.

Stability

The cosmetic compositions of the instant disclosure are stable, and ceramide NP is solubilized. With respect to stability, in certain embodiments, the cosmetic compositions do not visually phase separate or form visibly observable particulates for at least 2 weeks, 4 weeks, and/or 8 weeks in storage at 4° C., 25° C., 37° C., and/or 45° C.

In another embodiment, the cosmetic compositions do not visually phase separate or form visibly observable particulates for at least 10 cycles of freeze-thaw testing, wherein the freeze-thaw testing comprises placing the cosmetic composition in a stability chamber and subjecting it to temperature fluctuation at 12-hour intervals, for a first interval of 12 hours at −20° C. followed by a second interval of 12 hours at 25° C.

In another embodiment, the viscosity of the cosmetic compositions does not change by more than 20%, 15%, 10%, or 5%, for at least 2 weeks, 4 weeks, and/or 8 weeks in storage at 4° C., 25° C., 37° C., and/or 45° C.

With respect to ceramide NP, in various embodiments, at least 80%, 85%, 90%, 95%, or 98% of ceramide NP remains solubilized a for at least 2 weeks, 4 weeks, and/or 8 weeks in storage at 4° C., 25° C., 37° C., and/or 45° C. The lack of visually observable phase separation and particulate formation (discussed above) also shows that the ceramide NP remains solubilized.

Viscosity

In general, the cosmetic compositions of the instant case have a viscosity of about 5,000 to about 200,000 Pa·s at 25° C., and shear rate of 1 $s^{-1}$ at 25° C. However, the cosmetic compositions may have a viscosity of about 10,000 to about 200,000 Pa·s, about 10,000 to about 180,000 Pa·s, about 10,000 to about 150,000 Pa·s, about 10,000 to about 120,000 Pa·s, about 15,000 to about 200,000 Pa·s, about 15,000 to about 180,000 Pa·s, about 15,000 to about 150,000 Pa·s, about 15,000 to about 120,000 Pa·s, about 20,000 to about 200,000 Pa·s, about 20,000 to about 180,000 Pa·s, about 20,000 to about 150,000 Pa·s, about 20,000 to about 120,000, about 50,000 to about 200,000 Pa·s, about 50,000 to about 180,000 Pa·s, about 50,000 to about 150,000 Pa·s, about 50,000 to about 120,000 Pa·s, about 70,000 to about 200,000 Pa·s, about 70,000 to about 180,000 Pa·s, about 70,000 to about 150,000 Pa·s, about 70,000 to about 120,000 Pa·s, or about 70,000 to about 100,000 Pa·s at 25° C., and shear rate of 1 $s^{-1}$ at 25° C.

The viscosity measurements can be carried out, for example, using a Broooksfield viscometer/rheometer using a t-bar spindle at a speed of 5, 10, 15, and/or 20 rpm. An RVDV-II+Pro Viscometer with RheocalcT software may be employed for automated instrument control and data acquisition. The test temperature is maintained at 25° C. by using a Brookfield TC-502P Programmable Refrigerated Bath. From its original container, a sample is transferred into a 120 mL glass jar and then tested.

Methods

The instant disclosure relates to methods of treating skin. The methods include applying a cosmetic composition according to the instant disclosure, optionally allowing the cosmetic composition to remain on the skin for a period of time. The cosmetic compositions are typically applied directly to the skin using the hand or a cloth. The skin may be optionally washed or rinsed prior to application. The method for treating the skin can be carried out once daily or may be carried out multiple times. For example, the method for treating skin may be carried out once daily, twice daily, weekly, bi-weekly for an extended period of time, for example, for about 1, 2, 3, 4, 5, or 6 months up to 1 year, or longer.

In various embodiments, the methods hydrate the skin and/or provide maintenance of moisture balance, alleviate/reduce itching, chronic dryness, peeling, and scaling; and improve the natural lipid barrier of skin, which helps treat dry and aging skin. In further embodiments, when the compositions includes hydroxypropyl tetrahydropyrantriol, the methods reduce the appearance of fine lines and wrinkles, improve production of hyaluronic acid via stimulation of glycosaminoglycan (GAG) synthesis, softening of stratum corneum to relieve cumulative stress on the epidermis and dermis, etc.

In certain embodiments, the method further comprises mixing a cosmetic composition of the instant disclosure with one or more additional cosmetic compositions prior to application to the skin. For example, the cosmetic composition of the instant disclosure can be mixed with one or more additional cosmetic compositions immediately prior to application to the skin, for example, the mixing may occur within 1 minute, 2 minutes, 5 minutes, 10 minutes, 15 minutes, or 30 minutes prior to application to the skin. In certain embodiments, the cosmetic compositions can be mixed in an individual's hands prior to applying the mixture to the skin, for example, the skin of the face.

The instant disclosure also relates to methods for stabilizing cosmetic composition containing high amounts of ceramide NP. This method comprises combining ceramide NP according to the compositions of the instant case. The amounts of ceramide NP that may be included are the amounts set forth throughout the instant disclosure.

In various embodiments, the instant disclosure relates to methods for stabilizing cosmetic composition containing high amounts of ceramide NP. In various embodiments, the instant disclosure relates to preserving and/or stabilizing ceramide NP in cosmetic compositions. This results in cosmetic compositions containing high amounts of ceramide NP that preserve (maintain) and stabilize the high amounts of ceramide NP over time.

Kits

The cosmetic compositions of the instant disclosure may be provided in a kit, for example, a kit comprising an individually contained cosmetic composition according to the instant disclosure and one or more additional separately contained cosmetic compositions. In an embodiment, the one or more separately contained compositions may be an additional composition according to the instant disclosure or may be a different composition. The cosmetic compositions may be separately contained in different cartridges, which are included in a dispensing apparatus/device. In other words, the kit may be a dispensing apparatus/device comprising a plurality of cartridges in which the compositions are contained. The kit (or apparatus/device) may optionally dispense the cosmetic composition of the instant disclosure and separately dispense the one or more separately contained composition. In various embodiments, the compositions may be dispensed individually or concurrently, and may optionally be mixed (or not mixed) with each other prior to being dispensed. In an embodiment, the various compositions are not mixed with each other prior to being dispensed. Useful systems, cartridges, and dispensing apparatus/devices are disclosed in U.S. Pat. Nos. 9,968,177 and 9,808,071; US Patent Application Publication. Nos. 2021/0236390, 2021/0235849 and 2021/0236863; and in U.S. Ser. No. 17/162,555, which are all incorporated herein by reference in their entirety.

Embodiments

In certain embodiments the cosmetic compositions of the instant disclosure comprise or consist of:

(a) about 0.1 to about 5 wt. %, preferably about 0.1 to about 3 wt. %, more preferably about 0.2 to about 2 wt. %, even more preferably, about 0.3 to about 1.5 wt. % of ceramide NP;

(b) about 50 to about 90 wt. %, preferably about 55 to about 80 wt. %, more preferably about 55 to about 75 wt. % of water;

(c) about 0.5 to about 5 wt. %, more preferably about 0.5 to about 4 wt. %, even more preferably about 0.8 to about 3 wt. % of one or more first emulsifiers chosen from polyglycerol-based emulsifiers, preferably:

one or more polyglyceryl esters of C12-22 saturated, unsaturated and branched chain fatty acids, such as polyglyceryl-4 isostearate, polyglyceryl-3 oleate, polyglyceryl-2-sesquioleate, triglyceryl diisostearate, diglyceryl monooleate, tetraglyceryl monooleate, and mixtures thereof; and or one or more polyglyceryl methylglucose surfactants, such as polyglyceryl-3 methylglucose distearate, polyglyceryl-6 methylglucose distearate, polyglyceryl-10 methyl glucose distearate;

(d) about 0.5 to about 5 wt. %, more preferably about 0.5 to about 4 wt. %, even more preferably about 0.8 to about 3 wt. % of one or more second emulsifiers chosen from glyceryl esters having an HLB of about 3 to about 6, preferably chosen from bis-diglyceryl polyacyladipate-2, glyceryl behenate, glyceryl caprate, glyceryl cocoate, glyceryl erucate, glyceryl hydroxystearate, glyceryl isostearate, glyceryl lanolate, glyceryl laurate, glyceryl linoleate, glyceryl myristate, glyceryl oleate, glyceryl palmitate lactate, glyceryl sesquioleate, glyceryl stearate, glyceryl stearate citrate, glyceryl stearate lactate, glyceryl dioleate, glyceryl distearate, glyceryl laurate, and mixtures thereof, more preferably chosen from glyceryl stearate, bis-diglyceryl polyacyladipate, or a mixture thereof;

(e) about 0.5 to about 5 wt. %, preferably about 0.5 to about 4 wt. %, more preferably about 0.5 to about 3 wt. % of one or more third emulsifiers chosen from ethoxylated fatty acids, preferably derived from a fatty acid containing 8 to 24 carbon atoms and having from 2 to 200 molecules of ethylene oxide, more preferably chosen from polethoxylated stearic acid esters, for example, PEG-9 stearate, PEG-8 distearate, PEG-20 stearate, PEG-8 stearate, PEG-8 oleate, PEG-20 stearate, PEG-30 stearate, PEG-40 stearate, PEG-50 stearate, PEG-100 stearate, PEG-150 laurate, and mixtures therefore;

(f) about 0.2 to about 5 wt. %, preferably about 0.3 to about 4 wt. %, more preferably about 0.5 to about 3 wt. % of one or more fatty alcohols, preferably having from 10 to 30 carbon atoms, more preferably chosen from decyl alcohol, undecyl alcohol, dodecyl, myristyl, cetyl alcohol, stearyl alcohol, cetearyl alcohol, isostearyl alcohol, isocetyl alcohol, behenyl alcohol, linalool, oleyl alcohol, myricyl alcohol and a mixture thereof;

(g) about 4 to about 20 wt. %, preferably about 4 to about 15 wt. %, more preferably about 5 to about 10 wt. % of one or more non-triglyceride and non-aromatic fatty compounds, preferably chosen from fatty esters (e.g., isopropyl myristate, sorbitan isostearate), acyl sarcosinates, oils, alkanes (paraffins), fatty acids, fatty alcohol derivatives, fatty acid derivatives, waxes, lanolin, and mixtures thereof; preferably chosen from fatty esters acyl sarcosinates, and mixtures thereof;
(h) optionally, hydroxypropyl tetrahydropyrantriol, wherein if present, is preferably in an amount of about 10 to about 40 wt. %, more preferably about 10 to about 20 wt. %, and more preferably about 12 to about 18 wt. %;
(i) optionally, one or more thickening polymers, wherein if present, may be in an amount of about 0.01 to about 5 wt. %, preferably about 0.1 to about 4 wt. %, more preferably about 0.1 to about 3 wt. %, for example, polyacrylates (e.g., sodium polyacrylate), hydroxyethyl acrylate/sodium acryloyldimethyl taurate copolymer, ammonium acryloyldimethyltaurate/VP copolymer, acrylamide/sodium acryloyldimethyltaurate copolymer, polyacrylate crosspolymer-6, polyacrylamide, acrylatesc10-30 alkyl acrylate crosspolymer and mixtures thereof;
(j) optionally, one or more water-soluble solvents, wherein if present may be in an amount of about 1 to about 20 wt. %, preferably about 1 to about 15 wt. %, more preferably about 5 to about 15 wt. %, for example, glycerin, $C_2$-$C_6$ mono-alcohols, polyols (polyhydric alcohols), glycols, and a mixture thereof; and
(k) optionally, one or more miscellaneous ingredients, wherein if present, may be in an amount of about 0.01 to about 10 wt. %, preferably about 0.1 to about 8 wt. %, more preferably about 1 to about 6 wt. %, for example, miscellaneous ingredients chosen from miscellaneous emulsifiers/surfactants, preservatives, fragrances, pH adjusters, salts, antioxidants, vitamins, botanical extracts, UV filtering agents, proteins, protein hydrolysates and/or isolates, hydrotropes, pearlescent agents, fillers, colorants, mattifying agents, further skin active agents, buffers, and mixtures thereof;
wherein the composition is an oil-in-water emulsion and all percentages by weight are based on the total weight of the composition.

In addition to the various amounts for components (a) and (c)-(g) set forth above, in various embodiments it is preferably that the cosmetic compositions include one or more ratios relating to components (a) and (c)-(g) chosen from:
a weight ratio of the one or more first emulsifiers chosen from polyglycerol-based emulsifiers to the ceramide NP from about 1.5:1 to about 8:1 ((c):(a)), preferably about 1.5:1 to about 5:1, more preferably about 1.5:1 to about 3:1;
a weight ratio of the one or more second emulsifiers chosen from glyceryl esters having an HLB of about 3 to about 6 to the ceramide NP from about 0.8:1 to about 4:1 ((d):(a)), preferably 1:1 to about 3:1, more preferably about 1.2:1 to about 2.5:1;
a weight ratio of the one or more third emulsifiers chosen from ethoxylated fatty acids to the ceramide NP from about 0.7:1 to about 4:1 ((e):(a)), preferably about 0.8:1 to about 3:1, more preferably about 0.8:1 to about 2.5:1;
a weight ratio of the one or more fatty alcohols to the ceramide NP from about 0.7:1 to about 4:1 ((f):(a)), preferably about 0.8:1 to about 3:1, more preferably about 0.8:1 to about 2.5:1;
a weight ratio of the one or more non-triglyceride and non-aromatic fatty compounds to the ceramide NP from about 4:1 to about 20:1 ((g):(a)), preferably about 5:1 to about 15:1, more preferably about 6:1 to about 10:1.

In a preferred embodiment, the cosmetic compositions include the following ratios relating to all of components (a) and (c)-(g):
the weight ratio of the one or more first emulsifiers chosen from polyglycerol-based emulsifiers to the ceramide NP is from about 1.5:1 to about 8:1 ((c):(a)), preferably about 1.5:1 to about 5:1, more preferably about 1.5:1 to about 3:1;
the weight ratio of the one or more second emulsifiers chosen from glyceryl esters having an HLB of about 3 to about 6 to the ceramide NP to is from about 0.8:1 to about 4:1 ((d):(a)), preferably 1:1 to about 3:1, more preferably about 1.2:1 to about 2.5:1;
the weight ratio of the one or more third emulsifiers chosen from ethoxylated fatty acids to the ceramide NP is from about 0.7:1 to about 4:1 ((e):(a)), preferably about 0.8:1 to about 3:1, more preferably about 0.8:1 to about 2.5:1;
the weight ratio of the one or more fatty alcohols to the ceramide NP is from about 0.7:1 to about 4:1 ((f):(a)), preferably about 0.8:1 to about 3:1, more preferably about 0.8:1 to about 2.5:1; and
the weight ratio of the one or more non-triglyceride and non-aromatic fatty compounds to the ceramide NP is from about 4:1 to about 20:1 ((g):(a)), preferably about 5:1 to about 15:1, more preferably about 6:1 to about 10:1.

The cosmetic compositions of the instant disclosure are preferably stable, and ceramide NP is preferably solubilized. With respect to stability, in certain embodiments, the cosmetic compositions do not visually phase separate or form visibly observable particulates for at least 2 weeks, 4 weeks, and/or 8 weeks in storage at 4° C., 25° C., 37° C., and/or 45° C.

In another embodiment, the cosmetic compositions do not visually phase separate or form visibly observable particulates for at least 10 cycles of freeze-thaw testing, wherein the freeze-thaw testing comprises placing the cosmetic composition in a stability chamber and subjecting it to temperature fluctuation at 12-hour intervals, for a first interval of 12 hours at −20° C. followed by a second interval of 12 hours at 25° C.

In another embodiment, the viscosity of the cosmetic compositions does not change by more than 20%, 15%, 10%, or 5%, for at least 2 weeks, 4 weeks, and/or 8 weeks in storage at 4° C., 25° C., 37° C., and/or 45° C.

The cosmetic compositions preferably have a viscosity of about 5,000 to about 200,000 Pa·s at 25° C., and shear rate of 1 $s^{-1}$ at 25° C. However, the cosmetic compositions may have a viscosity of about 10,000 to about 200,000 Pa·s, about 10,000 to about 180,000 Pa·s, about 10,000 to about 150,000 Pa·s, about 10,000 to about 120,000 Pa·s, about 15,000 to about 200,000 Pa·s, about 15,000 to about 180,000 Pa·s, about 15,000 to about 150,000 Pa·s, about 15,000 to about 120,000 Pa·s, about 20,000 to about 200,000 Pa·s, about 20,000 to about 180,000 Pa·s, about 20,000 to about 150,000 Pa·s, about 20,000 to about 120,000, about 50,000 to about 200,000 Pa·s, about 50,000 to about 180,000 Pa·s, about 50,000 to about 150,000 Pa·s, about 50,000 to about 120,000 Pa·s, about 70,000 to about 200,000 Pa·s, about 70,000 to about 180,000 Pa·s, about 70,000 to about 150,000 Pa·s, about 70,000 to about 120,000 Pa·s, or about 70,000 to about 100,000 Pa·s at 25° C., and shear rate of 1 $s^{-1}$ at 25° C.

In certain embodiments the cosmetic compositions of the instant disclosure may comprise or consist of:
(a) about 0.5 to about 5 wt. %, preferably about 0.5 to about 3 wt. % of ceramide NP;
(b) about 50 to about 80 wt. %, preferably about 60 to 80 wt. % of water;
(c) about 0.1 to about 5 wt. %, preferably about 0.5 to about 4 wt. % of one or more first emulsifiers chosen from polyglyceryl 10-stearate, polyglyceryl-3-caprate, polyglyceryl-3-diisostearate, polyglyceryl-3 methylglucose distearate, and a mixture thereof;
(d) about 0.5 to about 5 wt. %, preferably about 0.5 to about 4 wt. %, more preferably about 0.5 to about 3 wt. % of one or more second emulsifiers chosen from glyceryl esters having an HLB of about 3 to about 10, for example, chosen from bis-diglyceryl polyacyladipate-2, glyceryl behenate, glyceryl caprate, glyceryl cocoate, glyceryl erucate, glyceryl hydroxystearate, glyceryl isostearate, glyceryl lanolate, glyceryl laurate, glyceryl linoleate, glyceryl myristate, glyceryl oleate, glyceryl palmitate lactate, glyceryl sesquioleate, glyceryl stearate, glyceryl stearate citrate, glyceryl stearate lactate, glyceryl dioleate, glyceryl distearate, glyceryl laurate, or a mixture thereof. In at least one instance the glyceryl ester comprises glyceryl stearate, bis-diglyceryl polyacyladipate, glyceryl ricinoleate, or a mixture thereof;
(e) about 0.5 to about 5 wt. %, preferably about 0.5 to about 4 wt. %, more preferably about 0.5 to about 3 wt. % of one or more third emulsifiers chosen from ethoxylated fatty acids having propylene oxide groups ranging from 40 to 100 and fatty chain of 8 to 24 carbon atoms, preferably polethoxylated stearic acid esters, for example, PEG-9 stearate, PEG-8 distearate, PEG-20 stearate, PEG-8 stearate, PEG-8 oleate, PEG-20 stearate, PEG-30 stearate, PEG-40 stearate, PEG-50 stearate, PEG-100 stearate, PEG-150 laurate, and mixtures therefore;
(f) about 0.2 to about 5 wt. %, preferably about 0.3 to about 4 wt. %, more preferably about 0.5 to about 3 wt. % of one or more fatty alcohols having from 8 to 24 carbon atoms, preferably chosen from decyl alcohol, undecyl alcohol, dodecyl, myristyl, cetyl alcohol, stearyl alcohol, cetearyl alcohol, isostearyl alcohol, isocetyl alcohol, behenyl alcohol, and a mixture thereof;
(g) about 4 to about 20 wt. %, preferably about 4 to about 15 wt. %, more preferably about 5 to about 10 wt. % of one or more non-triglyceride and non-aromatic fatty compounds chosen from fatty esters, acyl sarcosinates, or a mixture thereof;
(h) optionally, hydroxypropyl tetrahydropyrantriol, wherein if present, is preferably in an amount of about 10 to about 40 wt. %, more preferably about 10 to about 20 wt. %, and more preferably about 12 to about 18 wt. %;
(i) optionally, one or more thickening polymers, wherein if present, may be in an amount of about 0.01 to about 5 wt. %, preferably about 0.1 to about 4 wt. %, more preferably about 0.1 to about 3 wt. %, for example, polyacrylates (e.g., sodium polyacrylate), hydroxyethyl acrylate/sodium acryloyldimethyl taurate copolymer, ammonium acryloyldimethyltaurate/VP copolymer, acrylamide/sodium acryloyldimethyltaurate copolymer, polyacrylate crosspolymer-6, polyacrylamide, acrylatesc10-30 alkyl acrylate crosspolymer and mixtures thereof;
(j) about 1 to about 15 wt. % of one or more water-soluble solvents chosen from glycerin, $C_2$-$C_6$ mono-alcohols, polyols (polyhydric alcohols), glycols, and a mixture thereof; and
(k) optionally, one or more miscellaneous ingredients, wherein if present, may be in an amount of about 0.01 to about 10 wt. %, preferably about 0.1 to about 8 wt. %, more preferably about 1 to about 6 wt. %, for example miscellaneous ingredients chosen from miscellaneous emulsifiers/surfactants, preservatives, fragrances, pH adjusters, salts, antioxidants, vitamins, botanical extracts, UV filtering agents, proteins, protein hydrolysates and/or isolates, hydrotropes, pearlescent agents, fillers, colorants, mattifying agents, further skin active agents, buffers, and mixtures thereof;

wherein the composition is an oil-in-water emulsion and all percentages by weight are based on the total weight of the composition.

In addition to the various amounts for components (a) and (c)-(g) set forth above, in various embodiments it is preferably that the cosmetic compositions include one or more ratios relating to components (a) and (c)-(g) chosen from:

a weight ratio of the one or more first emulsifiers chosen from polyglycerol-based emulsifiers to the ceramide NP from about 1.5:1 to about 8:1 ((c):(a)), preferably about 1.5:1 to about 5:1, more preferably about 1.5:1 to about 3:1;

a weight ratio of the one or more second emulsifiers chosen from glyceryl esters having an HLB of about 3 to about 6 to the ceramide NP from about 0.8:1 to about 4:1 ((d):(a)), preferably 1:1 to about 3:1, more preferably about 1.2:1 to about 2.5:1;

a weight ratio of the one or more third emulsifiers chosen from ethoxylated fatty acids to the ceramide NP from about 0.7:1 to about 4:1 ((e):(a)), preferably about 0.8:1 to about 3:1, more preferably about 0.8:1 to about 2.5:1;

a weight ratio of the one or more fatty alcohols to the ceramide NP from about 0.7:1 to about 4:1 ((f):(a)), preferably about 0.8:1 to about 3:1, more preferably about 0.8:1 to about 2.5:1;

a weight ratio of the one or more non-triglyceride and non-aromatic fatty compounds to the ceramide NP from about 4:1 to about 20:1 ((g):(a)), preferably about 5:1 to 15:1, more preferably about 6:1 to 10:1.

In a preferred embodiment, the cosmetic compositions include the following ratios relating to all of components (a) and (c)-(g):

the weight ratio of the one or more first emulsifiers chosen from polyglycerol-based emulsifiers to the ceramide NP is from about 1.5:1 to about 8:1 ((c):(a)), preferably about 1.5:1 to about 5:1, more preferably about 1.5:1 to about 3:1;

the weight ratio of the one or more second emulsifiers chosen from glyceryl esters having an HLB of about 3 to about 6 to the ceramide NP to is from about 0.8:1 to about 4:1 ((d):(a)), preferably 1:1 to about 3:1, more preferably about 1.2:1 to about 2.5:1;

the weight ratio of the one or more third emulsifiers chosen from ethoxylated fatty acids to the ceramide NP is from about 0.7:1 to about 4:1 ((e):(a)), preferably about 0.8:1 to about 3:1, more preferably about 0.8:1 to about 2.5:1;

the weight ratio of the one or more fatty alcohols to the ceramide NP is from about 0.7:1 to about 4:1 ((f):(a)), preferably about 0.8:1 to about 3:1, more preferably about 0.8:1 to about 2.5:1; and the weight ratio of the one or more non-triglyceride and non-aromatic fatty compounds to the ceramide NP is from about 1:1 to about 20:1 ((g):(a)), preferably about 2:1 to 20:1, more preferably about 2:1 to 10:1.

The cosmetic compositions of the instant disclosure are preferably stable, and ceramide NP is preferably solubilized. With respect to stability, in certain embodiments, the cosmetic compositions do not visually phase separate or form visibly observable particulates for at least 2 weeks, 4 weeks, and/or 8 weeks in storage at 4° C., 25° C., 37° C., and/or 45° C.

In another embodiment, the cosmetic compositions do not visually phase separate or form visibly observable particulates for at least 10 cycles of freeze-thaw testing, wherein the freeze-thaw testing comprises placing the cosmetic composition in a stability chamber and subjecting it to temperature fluctuation at 12-hour intervals, for a first interval of 12 hours at −20° C. followed by a second interval of 12 hours at 25° C.

In another embodiment, the viscosity of the cosmetic compositions does not change by more than 20%, 15%, 10%, or 5%, for at least 2 weeks, 4 weeks, and/or 8 weeks in storage at 4° C., 25° C., 37° C., and/or 45° C.

The cosmetic compositions preferably have a viscosity of about 5,000 to about 200,000 Pa·s at 25° C., and shear rate of 1 s$^{-1}$ at 25° C. However, the cosmetic compositions may have a viscosity of about 10,000 to about 200,000 Pa·s, about 10,000 to about 180,000 Pa·s, about 10,000 to about 150,000 Pa·s, about 10,000 to about 120,000 Pa·s, about 15,000 to about 200,000 Pa·s, about 15,000 to about 180,000 Pa·s, about 15,000 to about 150,000 Pa·s, about 15,000 to about 120,000 Pa·s, about 20,000 to about 200,000 Pa·s, about 20,000 to about 180,000 Pa·s, about 20,000 to about 150,000 Pa·s, about 20,000 to about 120,000, about 50,000 to about 200,000 Pa·s, about 50,000 to about 180,000 Pa·s, about 50,000 to about 150,000 Pa·s, about 50,000 to about 120,000 Pa·s, about 70,000 to about 200,000 Pa·s, about 70,000 to about 180,000 Pa·s, about 70,000 to about 150,000 Pa·s, about 70,000 to about 120,000 Pa·s, or about 70,000 to about 100,000 Pa·s at 25° C., and shear rate of 1 s$^{-1}$ at 25° C.

EXAMPLES

As various changes could be made in the above-described methods without departing from the scope of the invention, it is intended that all matter contained in the above description and in the examples given below, shall be interpreted as illustrative and not in a limiting sense.

The following Examples are intended to be non-restrictive and explanatory only. The ingredient amounts in the compositions/formulas described below are expressed in % by weight, based on the total weight of the composition.

Example 1

(Cosmetic Compositions)

|  |  |  | Inventive | | Comparative | | | |
|---|---|---|---|---|---|---|---|---|
|  |  |  | A | B | C-1 | C-2 | C-3 | C-4 |
| (a) | Active | CERAMIDE NP (Ceramide 3) | 0.6 | 0.6 | 0.6 | 0.6 | 0.6 | 0.6 |
| (b) | Water | WATER | QS | QS | QS | QS | QS | QS |
| (c) | Polyglyceryl-Based Emulsifier | POLYGLYCERYL-3 METHYLGLUCOSE DISTEARATE | 1.0 | 1.0 |  | 1.0 | 1.0 | 1.0 |
| (d) | Glyceryl Ester Emulsifier | GLYCERYL STEARATE | 1.0 | 1.0 | 1.0 |  | 1.0 | 1.0 |
| (e) | Ethoxylated Fatty Acid Emulsifier | PEG-100 STEARATE | 0.5 | 0.5 | 0.5 | 0.5 |  | 0.5 |
| (f) | Fatty Alcohol | STEARYL ALCOHOL | 0.5 | 0.5 | 0.5 | 0.5 | 0.5 |  |
| (g) | Fatty Compouds | ISOPROPYL MYRISTATE, SORBITAN ISOSTEARATE, AND/OR ISOPROPYL LAUROYL SARCOSINATE | 4.3 | 4.3 | 4.3 | 4.3 | 4.3 | 4.3 |
| (h) | Active | HYDROXYPROPYL TETRAHYDROPYRANTRIOL | 15.0 | 15.0 | 15.0 | 15.0 | 15.0 | 15.0 |
| (i) | Thickening Polymer | SODIUM POLYACRYLATE, AMMONIUM ACRYLOYL-DIMETHYLTAURATE/VP COPOLYMER, AND/OR HYDROXYETHYL ACRYLATE/SODIUM ACRYLOYLDIMETHYL TAURATE COPOLYMER | 1.1 | 1.4 | 1.4 | 1.4 | 1.4 | 1.4 |
| (j) | Water-Soluble Solvent | PROPYLENE GLYCOL, AND/OR T-BUTYL ALCOHOL | 10.7 | 10.7 | 10.7 | 10.7 | 10.7 | 10.7 |
| (k) | Miscellaneous emulsifers/surfactants, salts, preservatives, pH adjusters, fragrances, colorants, chelants, and/or extracts, etc. | | ≤4 | ≤4 | ≤4 | ≤4 | ≤4 | ≤4 |
|  |  | Stable | Y | Y | NA | NA | NA | NA |
|  |  | Soluble (ceramide NP) below 95° C. | Y | Y | N | N | N | N |

Example 2

(Stability Studies)

Studies were carried out to determine the ceramide NP was solubilized below 95° C. To determine ceramide NP solubility, the components (a), (c), (d), (e), (f), and (g) were combined and heated to 95° C. with constant agitation. If the mixture became transparent below 95° C. it was solubilized initially. The mixtures were then added to a hot water phase (85-90° C.) (component (b)), homogenized, stirred, and allowed to cool. Solubility was monitored via microscope and macroscopic changes (e.g., grittiness). Inventive Compositions A and B solubilized the ceramide NP and are therefore designed with a "Y" (yes) for solubility in the table in Example 1. Comparative Compositions C-1 through C-4 did not solubilize the ceramide NP and are therefore designed with a "N" (no) for solubility in the table in Example 1. Because Comparative Compositions C-1 through C-4 did not solubilize the ceramide NP, these compositions were not subjected to further stability testing.

Inventive Compositions A and B of Example 1 were subjected to physical stability studies and visually evaluated for phase separation and assessed under a microscope for particulate formation. The compositions were analyzed upon initial manufacture of the composition ($T_0$). The compositions were again analyzed after 10 days of freeze-thaw testing. For freeze-thaw testing, the compositions were placed in a stability chamber and subjected to temperature fluctuation at 12-hour intervals. For 12 hours, the compositions were held at −20° C. For the next 12 hours, the compositions were held at 25° C. The cycle was repeated 10 times (for 10 days). Separately, the compositions of Example 1 were evaluated after 4 weeks (1 month) in storage at 4° C., 25° C., 37° C., and 45° C. and again at 8 weeks (2 months) at 4° C., 25° C., 37° C., and 45° C. and visually evaluated for phase separation and assessed under a microscope for particulate formation.

The inventive compositions were deemed stable ("Y") (yes) because they did not visually phase separate and did not form particulates.

The foregoing description illustrates and describes the invention. The disclosure shows and describes only the preferred embodiments but it should be understood that the invention is capable to use in various other combinations, modifications, and environments and is capable of changes or modifications within the scope of the inventive concepts as expressed herein, commensurate with the above teachings and/or the skill or knowledge of the relevant art. The embodiments described herein above are further intended to explain best modes known by applicant and to enable others skilled in the art to utilize the disclosure in such, or other, embodiments and with the various modifications required by the particular applications or uses thereof. Accordingly, the description is not intended to limit the invention to the form disclosed herein.

DEFINITIONS

As used herein, the terms "comprising," "having," and "including" (or "comprise," "have," and "include") are used in their open, non-limiting sense. The phrase "consisting essentially of" limits the scope of a claim to the specified materials or steps and those that do not materially affect the basic and novel characteristics of the claimed invention.

The terms "a," "an," and "the" are understood to encompass the plural as well as the singular.

Thus, the term "a mixture thereof" also relates to "mixtures thereof." Throughout the disclosure, if the term "a mixture thereof" is used, following a list of elements as shown in the following example where letters A-F represent the elements: "one or more elements selected from the group consisting of A, B, C, D, E, F, or mixtures thereof." The term, "a mixture thereof" does not require that the mixture include all of A, B, C, D, E, and F (although all of A, B, C, D, E, and F may be included). Rather, it indicates that a mixture of any two or more of A, B, C, D, E, and F can be included. In other words, it is equivalent to the phrase "one or more elements chosen from A, B, C, D, E, F, and a mixture of any two or more of A, B, C, D, E, and F."

Likewise, the term "a salt thereof" also relates to "salts thereof." Thus, where the disclosure refers to "an element selected from the group consisting of A, B, C, D, E, F, a salt thereof, or mixtures thereof," it indicates that that one or more of A, B, C, D, and F may be included, one or more of a salt of A, a salt of B, a salt of C, a salt of D, a salt of E, and a salt of F may be included, or a mixture of any two of A, B, C, D, E, F, a salt of A, a salt of B, a salt of C, a salt of D, a salt of E, and a salt of F may be included.

The salts referred to throughout the disclosure may include salts having a counter-ion such as an alkali metal, alkaline earth metal, or ammonium counterion. This list of counterions, however, is non-limiting. Appropriate counterions for the components described herein are known in the art.

The expression "one or more" means "at least one" and thus includes individual components as well as mixtures/combinations.

The term "plurality" means "more than one" or "two or more."

An "alkyl radical" is a linear or branched saturated hydrocarbon-based group, particularly $C_1$-$C_8$, more particularly $C_1$-$C_6$, preferably $C_1$-$C_4$ such as methyl, ethyl, isopropyl and tert-butyl;

An "alkoxy radical" is a alkyl-oxy wherein alkyl is as described herein before;

An "alkenyl radical" is a linear or branched unsaturated hydrocarbon-based group, particularly $C_2$-$C_8$, more particularly $C_2$-$C_6$, preferably $C_2$-$C_4$ such as ethylenyl, propylenyl;

An "alkylene radical" is a linear or branched divalent saturated $C_1$-$C_8$, in particular $C_1$-$C_6$, preferably $C_1$-$C_4$ hydrocarbon-based group such as methylene, ethylene or propylene.

Some of the various categories of components identified for the cosmetic compositions may overlap. In such cases where overlap may exist and the composition/product includes two overlapping components (or more than two overlapping components), an overlapping component does not represent more than one component. As an example, a fatty acid may be considered both a "non-triglyceride and non-aromatic fatty emollient" and a "surfactant/emulsifier." If a particular composition/product includes both a non-triglyceride and non-aromatic fatty emollient component and an surfactant/emulsifier component, a single type of fatty acid can serve as only a non-triglyceride and non-aromatic fatty emollient or a surfactant/emulsifier (a single fatty acid does not serve as both the non-triglyceride and non-aromatic fatty emollient component and the surfactant/emulsifier component).

All percentages, parts and ratios herein are based upon the total weight of the compositions of the present invention, unless otherwise indicated.

All ranges and values disclosed herein are inclusive and combinable. For examples, any value or point described herein that falls within a range described herein can serve as a minimum or maximum value to derive a sub-range, etc. Furthermore, all ranges provided are meant to include every specific range within, and combination of sub-ranges between, the given ranges. Thus, a range from 1-5, includes specifically points 1, 2, 3, 4 and 5, as well as sub-ranges such as 2-5, 3-5, 2-3, 2-4, 1-4, etc.; and points of 1, 2, 3, 4, and 5 includes ranges and sub-ranges of 1-5, 2-5, 3-5, 2-3, 2-4, 1-4, etc.

Other than in the operating examples, or where otherwise indicated, all numbers expressing quantities of ingredients and/or reaction conditions may be modified with the term "about," whether or not expressly stated.

Additionally, all numbers are intended to represent exact values as additional embodiments, whether or not modified by the term "about." For example, "an amount of about 1%" can be modified to refer to exactly 1%. As a further example, "an amount of 1%" can be modified to refer to "about 1%." Unless otherwise indicated, the term "about" is understood to encompass a range of +/−10% from the stated number. However, in some embodiments, the term may be defined to encompass narrower ranges, for example, +/−1%, 2%, 3%, 4%, 5%, 6%, 7%, 8%, 9%, and 10% from the stated number.

The term "surfactants" and "emulsifiers" include salts of the surfactants and emulsifiers even if not explicitly stated. In other words, whenever the disclosure refers to a surfactant or emulsifier, it is intended that salts are also encompassed to the extent such salts exist, even though the specification may not specifically refer to a salt (or may not refer to a salt in every instance throughout the disclosure), for example, by using language such as "a salt thereof" or "salts thereof." Sodium and potassium are common cations that form salts with surfactants and emulsifiers. However, additional cations such as ammonium ions, or alkanolammonium ions such as monoethanolammonium or triethanolammonium ions, may also form salts of surfactants.

The term "substantially free" or "essentially free" as used herein means the specific material may be present in small amounts that do not materially affect the basic and novel characteristics of the claimed invention. For instance, there may be less than 2% by weight of a specific material added to a composition, based on the total weight of the composition (provided that an amount of less than 2% by weight does not materially affect the basic and novel characteristics of the claimed invention). Similarly, a composition "substantially free" or "essentially free" of a stated material may include less than 1.5 wt. %, less than 1 wt. %, less than 0.5 wt. %, less than 0.1 wt. %, less than 0.05 wt. %, or less than 0.01 wt. %, or none of the specified material. The term "substantially free" or "essentially free" as used herein may also mean that the specific material is not added to the composition but may still be present in a raw material that is included in the composition.

Furthermore, all components that are positively set forth in the instant disclosure may be negatively excluded from the claims, e.g., a claimed composition may be "free," "essentially free" (or "substantially free") of one or more components that are positively set forth in the instant disclosure. As an example, Silicones can optionally be included in the cosmetic compositions but preferably the compositions are free or essentially free from silicones. Silicones are synthetic polymers made up of repeating units of siloxane, elemental silicon and oxygen, combined with other elements, most often carbon and hydrogen. Thus, silicones are also called polysiloxanes. In some instances, the cosmetic compositions of the instant case can be free or essentially free from dimethicones, amomdimethicones, dimethiconols, cyclosiloxanes, siloxanes, etc.

All publications and patent applications cited in this specification are herein incorporated by reference, and for any and all purposes, as if each individual publication or patent application were specifically and individually indicated to be incorporated by reference. In the event of an inconsistency between the present disclosure and any publications or patent application incorporated herein by reference, the present disclosure controls.

The invention claimed is:

1. A cosmetic composition comprising:
   (a) about 0.5 to about 5 wt. % of ceramide NP;
   (b) about 50 to about 80 wt. % of water;
   (c) one or more first emulsifiers chosen from polyglycerol-based emulsifiers,
       wherein (c) and (a) are in a weight ratio of about 1.5:1 to about 8:1 ((c):(a));
   (d) one or more second emulsifiers chosen from glyceryl esters having an HLB (hydrophilic-lipophilic balance) of about 3 to about 6,
       wherein (d) and (a) are in a weight ratio of about 0.8:1 to about 4:1 ((d):(a));
   (e) one or more third emulsifiers chosen from ethoxylated fatty acids,
       wherein (e) and (a) are in a weight ratio of about 0.7:1 to about 4:1 ((e):(a));
   (f) one or more fatty alcohols,
       wherein (f) and (a) are in a weight ratio of 0.7:1 to about 4:1 ((f):(a)); and
   (g) one or more non-triglyceride and non-aromatic fatty compounds;
       wherein the composition is an oil-in-water emulsion,
       all percentages by weight are based on a total weight of the composition, and
       the composition does not visually phase separate or form visibly observable particulates for at least 8 weeks in storage at 4° C. and 45° C.

2. The composition of claim 1, wherein the polyglycerol-based emulsifiers are chosen from polyglyceryl 10-stearate, polyglyceryl-3-caprate, polyglyceryl-3-diisostearate, polyglyceryl-3 methylglucose distearate, or mixtures thereof.

3. The composition of claim 1, wherein the glyceryl esters having an HLB of about 3 to about 6 are chosen from bis-diglyceryl polyacyladipate-2, glyceryl behenate, glyceryl erucate, glyceryl hydroxystearate, glyceryl isostearate, glyceryl lanolate, glyceryl laurate, glyceryl linoleate, glyceryl myristate, glyceryl oleate, glyceryl palmitate lactate, glyceryl sesquioleate, glyceryl stearate, citrate, glyceryl dioleate, glyceryl distearate, glyceryl laurate, or mixtures thereof.

4. The composition of claim 1, wherein the ethoxylated fatty acids have ethylene oxide groups ranging from 40 to 100 and fatty chain of 12 to 24 carbon atoms.

5. The composition of any claim 1, wherein the fatty alcohols have from 12 to 24 carbon atoms.

6. The composition of claim 1, wherein the fatty alcohols are chosen from cetyl alcohol, stearyl alcohol, cetearyl alcohol, behenyl alcohol, lauryl alcohol, myristic or myristyl alcohol, arachidyl alcohol, lignoceryl alcohol, or mixtures thereof.

7. The composition of claim 1, wherein the one or more non-triglyceride and non-aromatic fatty compounds are chosen from fatty esters, acyl sarcosinates, polyolefins, waxes, squalane, squalene, hydrogenated polyisobutene, hydrogenated polydecene, polybutene, mineral oil, pentahydrosqualene, plant and/or vegetable oil, hydrocarbon-based oils, or mixtures thereof.

8. The composition of claim 7, wherein the one or more non-triglyceride and non-aromatic fatty compounds are chosen from fatty esters, acyl sarcosinates, or mixtures thereof.

9. The composition of claim 1, further comprising:
(h) hydroxypropyl tetrahydropyrantriol.

10. The composition of claim 9, wherein the hydroxypropyl tetrahydropyrantriol is in an amount from about 10 to about 40 wt. %, based on the total weight of the composition.

11. The composition of claim 1, further comprising:
(i) about 0.1 to about 5 wt. % of one or more thickening polymers.

12. The composition of claim 10, wherein the one or more thickening polymers are chosen from polyacrylates, hydroxyethyl acrylate/sodium acryloyldimethyl taurate copolymer, ammonium acryloyldimethyltaurate/VP copolymer, acrylamide/sodium acryloyldimethyltaurate copolymer, polyacrylate crosspolymer-6, polyacrylamide, acrylates C10-30 alkyl acrylate crosspolymer, or mixtures thereof.

13. The composition of claim 1, further comprising:
(j) about 5 to about 15 wt. % of one or more water-soluble solvents.

14. The composition of claim 13, wherein the one or more water-soluble solvents are chosen from glycerin, $C_2$-$C_6$ mono-alcohols, polyols, glycols, or mixtures thereof.

15. The composition of claim 1 having a pH of about 5 to about 7.

16. The composition of claim 1 having a viscosity of about 20,000 to about 80,000 Pa·s at 25° C., and shear rate of 1 $s^{-1}$ at 25° C.

17. A cosmetic composition comprising:
(a) about 0.5 to about 5 wt. % of ceramide NP;
(b) about 50 to about 80 wt. % water;
(c) about 0.1 to about 5 wt. % of one or more first emulsifiers chosen from polyglyceryl 10-stearate, polyglyceryl-3-caprate, polyglyceryl-3-diisostearate, polyglyceryl-3 methylglucose distearate, or mixtures thereof;
(d) about 0.1 to about 5 wt. % of one or more second emulsifiers chosen from bis-diglyceryl polyacyladipate-2, glyceryl behenate, glyceryl caprate, glyceryl cocoate, glyceryl erucate, glyceryl hydroxystearate, glyceryl isostearate, glyceryl lanolate, glyceryl laurate, glyceryl linoleate, glyceryl myristate, glyceryl oleate, glyceryl palmitate lactate, glyceryl sesquioleate, glyceryl stearate, glyceryl stearate citrate, glyceryl stearate lactate, glyceryl dioleate, glyceryl distearate, glyceryl laurate, or mixtures thereof;
(e) about 0.1 to about 5 wt. % of one or more third emulsifiers chosen from ethoxylated fatty acids having ethylene oxide groups ranging from 40 to 100 and fatty chain of 8 to 24 carbon atoms;
(f) about 0.2 to about 5 wt. % of one or more fatty alcohols having from 8 to 24 carbon atoms;
(g) about 1 to about 10 wt. % of one or more non-triglyceride and non-aromatic fatty compounds chosen from fatty esters, acyl sarcosinates, or mixtures thereof; and
(h) about 10 to about 20 wt. % of hydroxypropyl tetrahydropyrantriol;
(i) optionally, one or more thickening polymers;
(j) about 0.1 to about 10 wt. % of one or more water-soluble solvents chosen from glycerin, $C_2$-$C_6$ mono-alcohols, polyols, glycols, or mixtures thereof;
wherein the composition is an oil-in-water emulsion and all percentages by weight are based on the total weight of the composition.

18. A method for treating skin comprising applying the cosmetic composition of any one of claim 1 to the skin.

19. A cosmetic composition comprising:
(a) about 0.5 to about 2 wt. % of ceramide NP;
(b) about 50 to about 80 wt. % of water;
(c) one or more first emulsifiers chosen from polyglycerol-based emulsifiers chosen from polyglyceryl 10-stearate, polyglyceryl-3-caprate, polyglyceryl-3-diisostearate, polyglyceryl-3 methylglucose distearate, or mixtures thereof,
wherein (c) and (a) are in a weight ratio of about 1.5:1 to about 3:1 ((c):(a));
(d) one or more second emulsifiers chosen from glyceryl esters chosen from bis-diglyceryl polyacyladipate-2, glyceryl behenate, glyceryl erucate, glyceryl hydroxystearate, glyceryl isostearate, glyceryl lanolate, glyceryl laurate, glyceryl linoleate, glyceryl myristate, glyceryl oleate, glyceryl palmitate lactate, glyceryl sesquioleate, glyceryl stearate, citrate, glyceryl dioleate, glyceryl distearate, glyceryl laurate, or mixtures thereof,
wherein (d) and (a) are in a weight ratio of about 1.2:1 to about 2.5:1 ((d):(a));
(e) one or more third emulsifiers chosen from ethoxylated fatty acids,
wherein (e) and (a) are in a weight ratio of about 0.8:1 to about 2.5:1 ((e):(a));
(f) one or more fatty alcohols having from 12 to 24 carbon atoms,
wherein (f) and (a) are in a weight ratio of 0.8:1 to about 2.5:1 ((f):(a)); and
(g) one or more non-triglyceride and non-aromatic fatty compounds;
wherein the composition is an oil-in-water emulsion,
all percentages by weight are based on a total weight of the composition, and
the composition does not visually phase separate or form visibly observable particulates for at least 8 weeks in storage at 4° C. and 45° C.

20. The composition of claim 19 having a viscosity of about 20,000 to about 80,000 Pa·s at 25° C., and shear rate of 1 $s^{-1}$ at 25° C.

* * * * *